(12) United States Patent
Khair

(10) Patent No.: US 9,451,920 B2
(45) Date of Patent: Sep. 27, 2016

(54) SYSTEM AND METHOD FOR MONITORING ARTERIAL AND VENOUS BLOOD OXYGEN, BLOOD GLUCOSE, AND BLOOD CONSTITUENT CONCENTRATION

(71) Applicant: Mohammad Khair, Irvine, CA (US)

(72) Inventor: Mohammad Khair, Irvine, CA (US)

(*) Notice: Subject to any disclaimer, the term of this patent is extended or adjusted under 35 U.S.C. 154(b) by 416 days.

(21) Appl. No.: 13/949,500

(22) Filed: Jul. 24, 2013

(65) Prior Publication Data

US 2015/0031969 A1 Jan. 29, 2015

Related U.S. Application Data

(60) Provisional application No. 61/700,892, filed on Sep. 14, 2012.

(51) Int. Cl.

| | |
|---|---|
| A61B 5/0205 | (2006.01) |
| A61B 5/021 | (2006.01) |
| A61B 5/145 | (2006.01) |
| A61B 5/026 | (2006.01) |
| A61B 5/00 | (2006.01) |
| A61B 5/1455 | (2006.01) |
| A61B 5/0295 | (2006.01) |
| A61N 1/365 | (2006.01) |
| A61N 1/39 | (2006.01) |
| A61M 1/14 | (2006.01) |
| A61M 1/10 | (2006.01) |
| A61B 5/02 | (2006.01) |
| A61B 5/029 | (2006.01) |
| A61M 5/172 | (2006.01) |
| A61B 5/0402 | (2006.01) |
| A61B 5/024 | (2006.01) |
| A61M 16/01 | (2006.01) |
| A61B 5/0215 | (2006.01) |

(52) U.S. Cl.
CPC ............. *A61B 5/7239* (2013.01); *A61B 5/021* (2013.01); *A61B 5/026* (2013.01); *A61B 5/029* (2013.01); *A61B 5/02028* (2013.01); *A61M 1/1086* (2013.01); *A61M 1/14* (2013.01); *A61N 1/36585* (2013.01); *A61N 1/3987* (2013.01); *A61B 5/0205* (2013.01); *A61B 5/0215* (2013.01); *A61B 5/02055* (2013.01); *A61B 5/0261* (2013.01); *A61B 5/0295* (2013.01); *A61B 5/02108* (2013.01); *A61B 5/02433* (2013.01); *A61B 5/0402* (2013.01); *A61B 5/14532* (2013.01); *A61B 5/14546* (2013.01); *A61B 5/14551* (2013.01); *A61B 5/14552* (2013.01); *A61B 5/726* (2013.01); *A61B 5/7225* (2013.01); *A61B 5/7257* (2013.01); *A61B 5/742* (2013.01); *A61M 5/1723* (2013.01); *A61M 16/01* (2013.01); *A61M 2230/005* (2013.01); *A61M 2230/42* (2013.01)

(58) Field of Classification Search
CPC ............ A61B 5/14532; A61B 5/1455; A61B 5/1495; A61B 5/1459; A61B 5/14546
See application file for complete search history.

(56) References Cited

U.S. PATENT DOCUMENTS

| | | | | |
|---|---|---|---|---|
| 2004/0059209 | A1* | 3/2004 | Al-Ali | A61B 5/746 600/323 |
| 2008/0077022 | A1* | 3/2008 | Baker | A61B 5/02416 600/500 |
| 2009/0326393 | A1* | 12/2009 | Sethi | A61B 5/021 600/494 |
| 2012/0065528 | A1* | 3/2012 | Gill | A61B 5/02028 600/509 |
| 2012/0150002 | A1* | 6/2012 | Shelley | A61B 5/7278 600/323 |
| 2012/0239104 | A1* | 9/2012 | Rosenberg | A61B 5/02028 607/20 |

* cited by examiner

*Primary Examiner* — Tse Chen
*Assistant Examiner* — Yoojin Lee
(74) *Attorney, Agent, or Firm* — Davis Chin

(57) ABSTRACT

A system for measuring of arterial and venous blood constituent concentration based first on measuring cardiac blood flow balance parameter between the right chamber of the heart and the left chamber of the heart, which includes a sensor device for measuring one of blood pressure and blood flow rate and blood constituent concentration of a patient so as to generate an arterial pulse signal. A processing unit is responsive to the arterial pulse signal for generating full arterial pulse plethysmography waveforms, arterio-venous pulse plethysmography waveforms, and balance parameters. A computational device that is responsive to plethysmography waveforms generating a plurality of state space linear transfer functions by applying system identification between plethysmography waveforms at various wavelengths representing a plurality of models of the blood constituent concentration, including oxygen, carbon dioxide, hemoglobin, and glucose, and displaying related useful information.

7 Claims, 16 Drawing Sheets

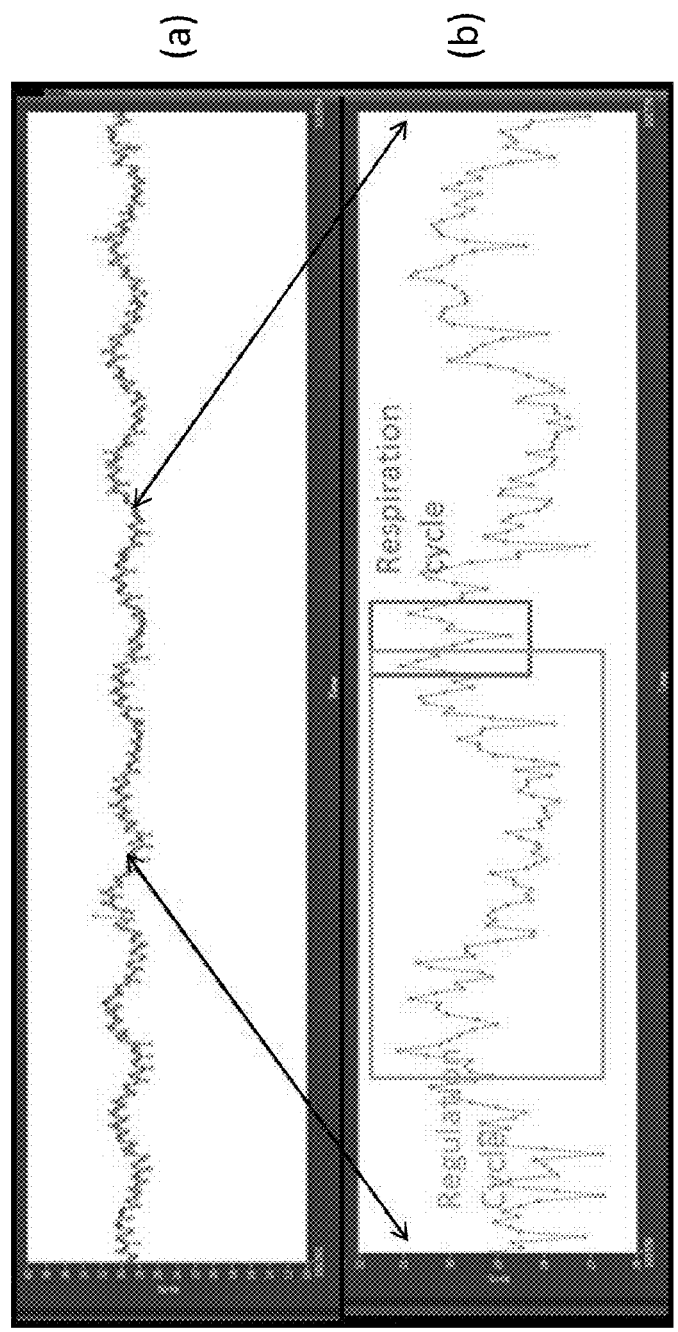

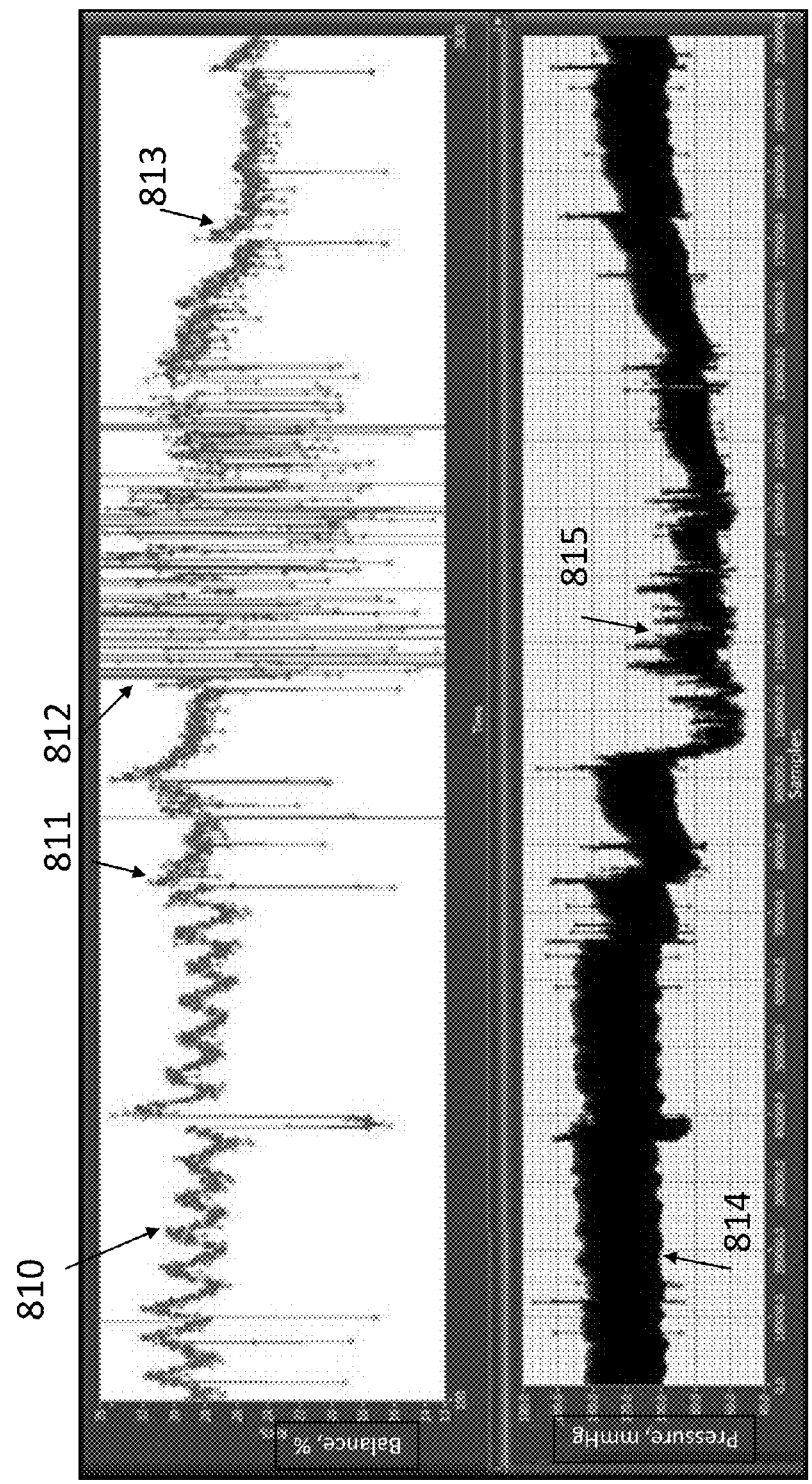

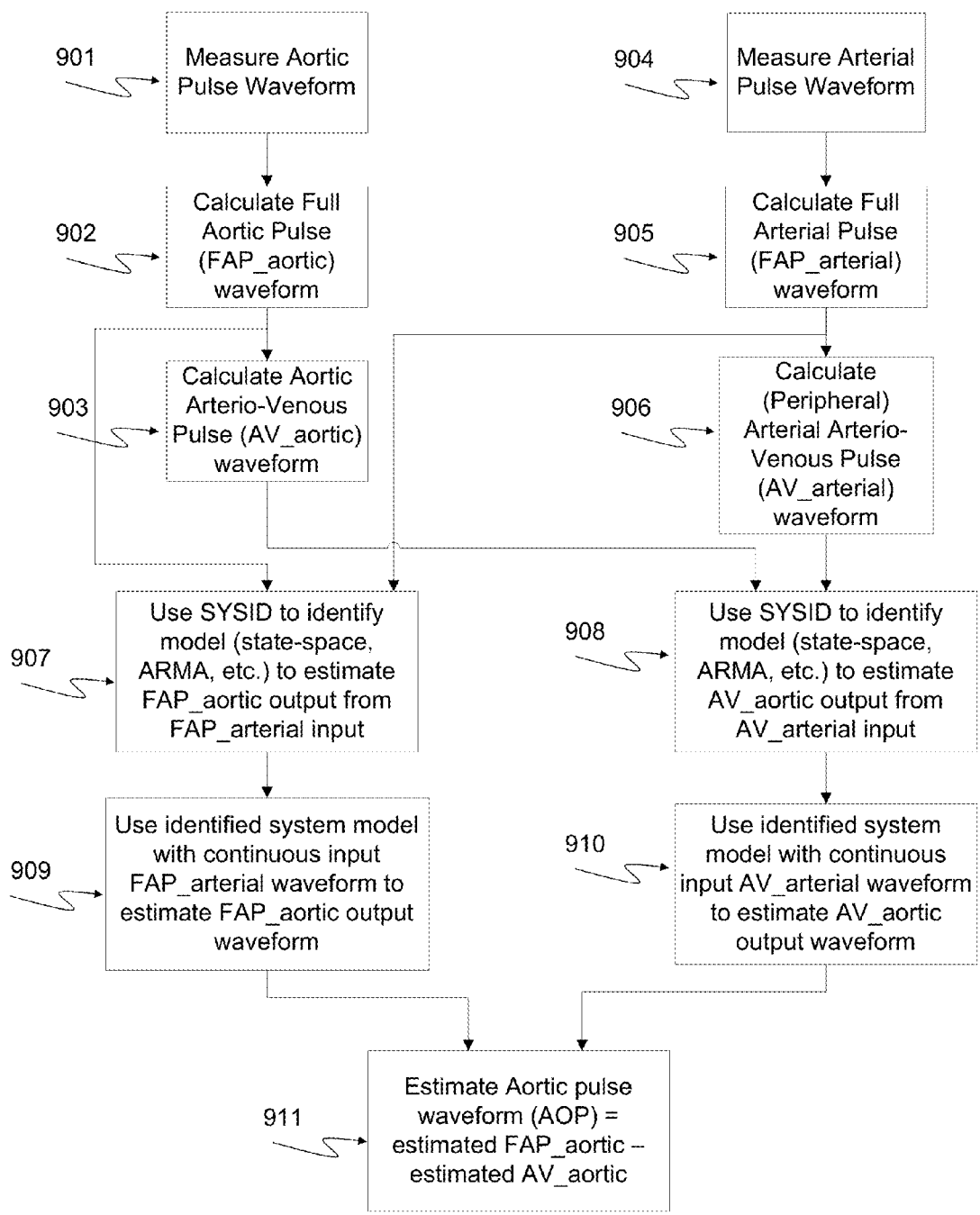

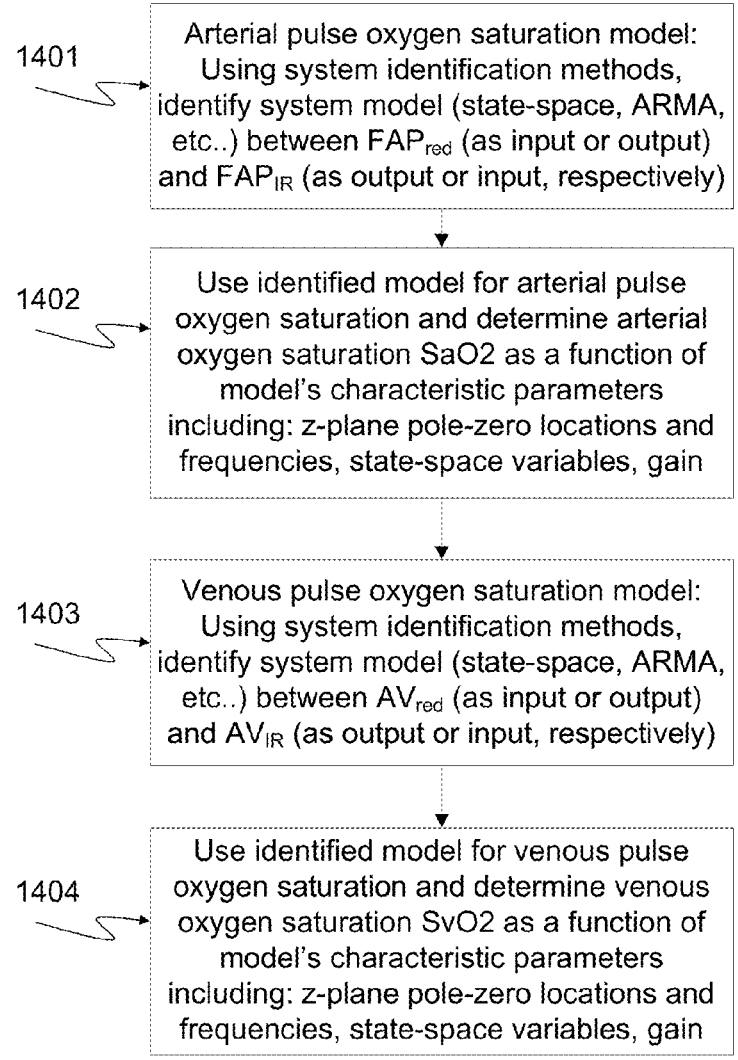

SYSTEM AND METHOD FOR MONITORING ARTERIAL AND VENOUS BLOOD OXYGEN, BLOOD GLUCOSE, AND BLOOD CONSTITUENT CONCENTRATION

CROSS-REFERENCE TO RELATED APPLICATIONS

This application is a non-provisional application which claims the benefits of provisional application Ser. No. 61/700,892 filed on Sep. 14, 2012.

BACKGROUND OF THE INVENTION

1. Technical Field

This invention relates generally to methods, devices, and systems used in the field of cardiovascular medicine for clinically assessing of a patient's health condition. More particularly, it relates to a new and improved system and method for monitoring cardiac blood flow balance between the right and left heart chambers based on arterial pulse waveforms representing blood pressure or flow or constituent concentration per cardiac cycle.

The description below is merely provided for general background information and for assisting in understanding the technical field to which the present invention is related. As is generally known in the art, the circulatory system in human beings is responsible for transporting oxygen and other nutrients to the cells of the human body. The circulatory system includes a heart, arteries, capillaries, and veins. In a healthy patient, the heart pumps blood with a certain pressure and volume so as to ensure that proper blood circulation is realized within the human body. Therefore, a discussion of the blood flow in the heart and congestive heart failure (CHF) will now be provided initially.

With attention directed to FIG. 1 of the drawings which is labeled "Prior Art", there is illustrated a diagram of the cardio-vascular system and its cycle. The heart 2 consists of four chambers; namely, the right atria 4, the right ventricle 6, the left atria 8 and the left ventricle 10. The right atria 4 receives carbon dioxide-filled blood which is returning from the body through the superior vena cava 12 and the inferior vena cava 14 where they join in the central venous. The right ventricle 6 receives the blood from the right atria 4 via a tricuspid valve 16 located between the two chambers. The right ventricle 6 pumps the blood via a pulmonary valve 22 into the pulmonary artery 18 which branches into the right pulmonary artery 18($a$) for carrying the blood to the right lung 20($a$), and the left pulmonary artery 18($b$) for carrying the blood to the left lung 20($b$). After receiving oxygen in the lungs 20($a$) and 20($b$), the oxygen-filled blood is returned to the left atria 8 of the heart 2 via the right pulmonary vein 24($a$) and the left pulmonary vein 24($b$). The blood is then passed into the left ventricle 10 via mitral valve 26. Next, the left ventricle 10 pumps the blood via the aortic valve 30 into the aorta 28 which branches into the ascending aorta for delivery throughout the upper body 31($a$) heads and arms, and the descending aorta 31($b$) for delivery throughout the lower body including the trunk and legs via the network of arteries, capillaries, and finally returned to the heart 2 via the superior vena cava 12 and the inferior vena cava 14, which both merge into the center venous 32. Both the right atria 4 and the left atria 8 pump simultaneously, and both the right ventricle 6 and the left ventricle 10 pump simultaneously. In every pumping cycle, each chamber undergoes an expansion cycle called diastole followed by a contraction cycle called systole. On the ECG waveform, the Atrial diastolic phase extends between the S in the QRS complex until the start of the following P wave, while atrial systole is between the start of the P wave and extends through the following S in the QRS complex. Similarly, the Ventricular systolic phase is between the R in QRS-complex and the following end of the T-wave, while ventricular diastolic phase is between end of the T-wave and the following R in the QRS-complex. The atrial systolic phase occurs mostly during ventricular diastolic phase with a small fractional overlap to ventricular systole, while the atrial diastolic phase starts with the ventricular systolic phase but also extends and overlaps a substantial portion of the ventricular diastolic phase. Atrial diastolic phase has a longer duty cycle as compared to Atrial systolic phase.

The left ventricle (LV) and the right atrium (RA) are connected in a supply and demand relationship. Also the right ventricle (RV) and the left atrium (LA) are connected in a supply and demand relationship. A balance therefore must be achieved for each supply and demand relationship between the LV and RA (termed Left Right Balance (LRB)), and between the RV and LA (termed Right Left Balance (RLB)). Similarly a balance must be achieved across the two pairs of supply and demand relationships (LV,RA) and (RV,LA). Such a balance of the LRB and RLB balance parameters is termed the Systemic-Pulmonary circulation balance parameter (SPB) indicating a shift of the blood supply towards the systemic portion of the circulatory cycle or the pulmonary portion of the circulatory cycle. When the SPB is normal, this can be used to validate assumptions of the Fick equation that the left and right ventricular cardiac output on average are equivalent, as presumed in healthy individuals.

In healthy human beings, the right heart's cardiac output (RCO) blood flow is presumed equivalent to the left heart's cardiac output (LCO), on average, since the cycle must maintain steady blood flow through out the circulatory system. However, this is not true in patients with certain types of heart disease. For example, an infarction or arrhythmia on one side of the heart may lead to insufficiency in balance between the RCO and LCO. Thus, cardiac output (CO) is an important indicator not only for the diagnosis of the certain types of heart disease, but also for the continuous monitoring of a patient's health condition.

One basis for most common cardiac output-measurement systems is given by the well-known equation CO=HR×SV, wherein CO is the cardiac output defined as blood flow in liters/min and is equal to the heart rate (HR) times the stroke volume (SV). The stroke volume is usually measured in liters, and the heart rate is usually measured in beats per minute. This equation explains that the amount of blood the heart pumps out over a unit of time (e.g., a minute) is simply equal to the amount it pumps out on every beat (stroke) times the number of beats per time unit.

If the right heart's cardiac output RCO (blood flow out of the right ventricle into the pulmonary artery) mostly exceeds the left heart's cardiac output LCO (blood flow out of the left ventricle into the aorta) then blood accumulation in the pulmonary system (lungs) is evident, and which may lead to congestive heart failure (CHF). Similarly, if the left heart's cardiac output LCO mostly exceeds the right heart's cardiac output RCO then blood accumulation is evident in the body's vascular system and tissue fluids will accumulate leading to inflation in tissue or vascular diseases such as high blood pressure, and potentially may play a factor in the development of varicose veins. Therefore, a measure of the balance between the right heart's and left heart's cardiac outputs is necessary for monitoring the overall health of the cardiovascular and pulmonary systems.

In the inventor's view, the cardiac system is basically a control system with two primary objectives. The first primary objective is to maintain oxygen delivery to the tissue via adequate perfusion (blood flow and blood pressure), which is accomplished by varying the cardiac parameters such as heart rate, stroke volume, and contractility, and blood pressure. The heart's second primary objective is to maintain a target blood flow balance between the right and left heart chambers.

While the cardiac output balance between the right heart and the left heart chambers is an important clinical parameter for the purposes of diagnosing, treating, and monitoring cardiovascular disease, the conventional prior art techniques, such as thermodilution or dye dilution, for measuring this balance however requires intravascular or intramyocardial instrumentation which carries significant risks to the patient that includes increased perioperative morbidity and mortality, and increased long-term risks, such as stroke and pulmonary embolism. Additionally, intravascular instrumentation can only be performed by highly trained specialist which severely limits the availability of qualified physicians capable of implanting the device, thereby increasing the cost of the procedure.

Also, the estimation of the balance between right heart's and left heart's cardiac outputs by these conventional methods would necessitate measurement of both left and right cardiac outputs independently and then comparing (for example by subtraction or ratio or so any other means of comparison) both to obtain the measure of the balance. In addition, less invasive methods are also known in the prior art, but they have proved to be less accurate in their measurements. Further, the traditionally non-invasive methods are not able to distinguish between the left cardiac output and the right cardiac output.

2. Prior Art

In U.S. Pat. No. 5,211,177 to Chesney et al., there is disclosed a vascular impedance instrument which includes a transducer to obtain a digitized arterial blood pressure waveform. The digitized data is used to determine cardiac output and to subsequently obtain measurements of impedance parameters using the modified Windkessel model of the arterial system. The instrument is used as an aid in diagnosing, treating and monitoring patients with cardiovascular disease.

In U.S. Pat. No. 7,651,466 to Hatib, Feras et al., examines the pulse contour of arterial pressure pulses to map using an linear model (Windkessel method) into a flow pulse for purposes of estimating cardiac output. This does not take into account the relationships between the ventricular arterial supply and atrial venous demand on the shape of the pressure waveform, but it analyzes the segment component of waveform prior to the onset of the interaction of the atrial venous demand on the ventricular arterial supply. Calibration of the model compliance parameters are required for estimating the dynamic relationship between blood pressure and flow rate.

In U.S. Pat. No. 8,282,564 to Parlikar, et. al., Similarly uses a lumped compliance model to model (Windkessel method) the relationship between arterial pressure and flow rate to estimate cardiac output, again the interaction effects between the ventricular arterial supply and atrial venous demand are not considered on the shape or morphology of the arterial pressure waveform.

In EU Patent No. EP1,848,330 B1 to Bennett, Tommy, et. al. Uses right ventricular pressure (RVP) pulse contour to estimate the stroke volume using a Windkessel pulse contour method. This method uses the full dynamic waveform information in the RVP to relate to the stroke volume information. It does not selectively choose specific landmarks on the pressure waveform to relate to volume information in a static method as in this invention.

In U.S. Pat. No. 5,368,040 to James Carney, describes analysis of ventricular pressure waveform and derives landmarks identified from first and second derivative inflection points or zero-crossing points or as related to features on an ECG waveform. It does not attempt to map these pressure values to volumetric information for purposes of estimating cardiac volumes or flow rates given pressure information.

The determination of the oxygen content of the blood based on the spectral characteristics of hemoglobin and oxyhemoglobin. Wood (U.S. Pat. No. 2,706,927) described a method using two wavelengths of light. Shaw (U.S. Pat. No. 3,638,640) improved this procedure by using more wavelengths of light. This technique was made significantly more practical by use of the modulation caused by the pulse as invented in 1972 by Aoyagi (Japanese Application 947714, April 1979). Improvements were described by Nielsen (U.S. Pat. No. 4,167,331) and Flower (U.S. Pat. No. 4,863,265). These methods rely on the ratio (R) of normalized variable component of the red light to its infrared light counterpart to determine a ratio of absorbance due to hemoglobin color which is dependent on oxygen binding or saturation. The method suffers from sensitivity to motion artifacts, and inherent variability across subject's response curves. Calibration to empirically derived lookup table is necessary to map the R ratio to validated oxygen saturation values. This approach suffers from insufficiently describing the relationship between the red and infrared plethysmography waveforms and underestimates the model order and model structure that describe the dynamic relationship between the red and infrared signals, as it presumes the relationship as a simple linear scalar ratio factor R. It also only uses the measured arterial pulse waveform and does not apply the ratio R method to the arterial pulse primary components of arterial supply (represented by full arterial pulse) and venous demand (represented by arterio-venous pulse) waveforms as described herein.

The inventor of the instant invention, however, is not aware of system for measuring of a cardiac blood flow parameter between the left chamber of the heart and the right chamber of the heart that uses a sensor device to measure one of blood pressure and blood flow and blood constituent concentration of a patient so to generate an arterial pulse signal, a process unit for generating a full arterial pulse signal from the arterial pulse signal, the processor unit generating an arterio-venous pulse signal by subtracting the arterial pulse signal from the full arterial pulse signal, and the processor unit generating the balance parameter by calculating the ratio of the area under the curve of the arterio-venous pulse signal, measured by integration over the cardiac cycle, to the area under the curve of the full arterial pulse signal, measured by integration over the same cardiac cycle. The area under the curve can be calculated by the integration of the pulse waveform using any integration method, preferably trapezoidal approximation method. Whereas the DC offset can be either included in the integration, or normalized, or removed by subtraction. The use of the word pulse throughout herein is used to more generally indicate the measured signal of type such as a blood pressure or blood flow rate or blood constituent concentration waveform.

Therefore, it would be desirable to provide a system and method for measuring of a cardiac blood flow parameter between the left chamber of the heart and the right chamber of the heart useful in creating a clinical assessment of a patient's health condition. Further, it would be expedient that the system of the present invention be capable of performing as a clinically useful tool for the purpose of diagnosing, treating and monitoring the performance and function of a patient's liver, heart, lungs, brain, kidneys and other organs of the body. The present invention represents a significant improvement over the aforementioned prior art which is hereby incorporated by reference in their entirety.

BRIEF SUMMARY OF THE INVENTION

In broadest terms, a new and improved method is provided for the estimation of balance parameters between the right heart cardiac output and the left heart cardiac output based upon the analysis of the pulse wave of the arterial pulsation. The analysis includes the use of morphologic features of the Dicrotic Notch. The Dicrotic Notch is typically present throughout the Aortic arterial vasculature tree which is used to derive the Left-Right Balance (LRB) parameter. The Dicrotic Notch is also typically present throughout the Pulmonary Artery vasculature tree which is used to derive the Right-Left Balance (RLB) parameter.

The inventor has developed a new theory for explaining the morphology of the pulse wave of the arterial pulsation (arterial pulse pressure or flow waveforms) and specifically the occurrence of the Dicrotic Notch feature residing therein. The present invention is based upon the realization by the inventor that the morphology of an arterial pulse waveform lies in the circulatory nature of the blood in the vascular system. Most of the cardiac monitoring publications heretofore only analyzed either the left heart's performance or the right heart's performance without considering the interaction effects therebetween. In other words, the fact that the left and right heart cycles complement each other to complete the circulatory system was largely ignored.

The relationships between the right heart's cycle and the left heart's cycle cannot be ignored as there is a continuity of mass flow between them. Therefore blood flow, and subsequently characteristics of pressure behavior, on one side of the cycle must affect the other side of the cycle. The vascular pathways of arteries and veins are interconnected by the capillary bed which forms the connectivity between the right and left heart chambers, and establishes the interdependency and continuity between them in terms of blood flow. While blood pressure between the right and left heart chambers is not directly interdependent, because of the capillary bed therebetween, the blood flow is directly interdependent as it has to be continuous between the left and the right heart chambers. This direct relationship in blood flow results, as will be explained later, in an indirect blood pressure interdependency consequently. Although blood pressure pulse is related to blood flow pulse by an arterial compliance factor, a balance parameter expressed as a ratio of two pressure components will normalize out the effects of the compliance and therefore the ratio will be equivalent, at least from a trend perspective, to a balance parameter that is derived from a blood flow pulse measurement. Similarly, the blood constituent concentration dynamic variation on a per cardiac cycle basis is directly related to blood flow as the concentration will change based on the speed of the mass flow per unit time by the sensor. Therefore balance parameter trends derived from blood constituent concentration will be consistent in behavior to balance parameter trends derived from blood flow.

Often the performance of the left side of the vascular system is analyzed separately from the right side, which yields weak conclusions that cannot be generalized. Traditional models that failed to take into account the simultaneous effects of the left and right heart cycles tend to bias the attribution of the dynamics it models to one side over the other, and therefore fail to represent the true dynamics fully. The venous side of the blood system is acted upon by the right atrium (RA) pull the blood up towards the heart. Therefore, the RA actually applies a pull force (demand) on the venous blood flow. On the left heart's side, the left ventricle (LV) actually applies a push force (supply) on the arterial blood flow to force the blood through the capillary system into the tissues.

These two events occur substantially in simultaneous timing (in normal subjects) so that the left side's (LV) push is aided by the right side's (RA) pull, in order to facilitate the movement of blood throughout the capillary system in the tissues. The LV and the RA are interconnected by the vascular tree (arteries, veins, and capillaries). While the blood pressure in the venous side is substantially directly independent of the blood pressure on the arterial side as they are connected via the capillaries, the blood flow between the arterial and venous side is substantially directly dependent, as conservation of mass laws and continuity of flow must apply. In other words, in healthy subjects, whatever blood mass flow the venous side demands the arterial side must supply and vice versa to complete the circulatory system. In subjects with circulatory system disorders, in addition to blood in the vascular system, some fluids are either stored or extracted from tissue fluids or the interstitial space. Blood pressure is an equilibrium point to the demand and supply of blood (or blood flow). It is therefore important to view pressure in the context of such supply and demand forces on blood flow. This invention exploits the relationships of blood supply and demand to each other, and uses them to derive information about the arterial supply of blood from venous pulse information and about venous demand of blood from arterial pulse information.

In view of the foregoing background, it is therefore an object of the present invention to provide a system and method for measuring of cardiac blood flow balance parameter between the left chamber of the heart and the right chamber of the heart of improved design and performance. It is another object of the present invention to provide a system and method for clinically assessing of a patient's health condition based upon a balance parameter obtained by measured arterial pulse signal and assessing of the patient's health condition based upon the morphology of the balance signal. It is still another object of the present invention to provide a system and method for generating a full arterial pulse (FAP) signal, defined as the measured arterial pulse signal without the effect of atrial diastolic blood flow demand factor. The full arterial pulse (FAP) is defined by the measured arterial pulse signal without the effect of atrial diastolic blood flow demand, simulating an added component of arterio-venous (AV) pulse signal so as to result in a full arterial pulse signal (i.e representing ventricular supply factor without atrial interaction effects). It is still yet another object of the present invention to provide a system and method for measuring of cardiac blood flow balance parameter which utilizes system identification techniques for modeling a transfer function relationship between a peripheral artery AV pulse or FAP signal and an aortic AV pulse or FAP signal. It is still yet another object of the present invention to provide a system and method for measuring of cardiac blood flow balance parameter which utilizes system identification techniques for modeling a transfer function relationship between a pulmonary artery peripheral branch AV pulse or FAP signal and the pulmonary artery AV pulse or FAP signal.

These and other objects, features and advantages of the invention are provided by a system for measuring of cardiac blood flow balance between the left chamber of the heart and the right chamber of the heart which includes a sensing device for measuring one of blood pressure and blood flow and blood constituent concentration of a patient so as to generate an arterial pulse signal. A system identification technique is responsive to the arterial pulse signal for generating a full arterial pulse signal.

Advantageously, a processor unit is provided and is configured to produce an arterio-venous pulse signal defined by subtracting the arterial pulse signal from the full arterial pulse signal. Further, the processor unit computes a balance parameter by calculating the ratio of the areas under the curve, by integration over the cardiac cycle, for the arterio-venous (AV) pulse signal to the full arterial pulse (FAP) signal. Whereas the DC offset can be either included, or normalized, or removed by subtraction. In a preferred embodiment, a simple linear transfer function is established between these two signals such as an auto-regressive moving average model is computed using system identification methods. In another preferred embodiment, a generalized state-space linear model of the balance parameter relationship between these two signals is computed using system identification methods.

In addition, a computational device generates a set of physiological parameters from the balance parameter. A display monitor receives the set of physiological parameters from the computational device for displaying meaningful information to indicate a clinical assessment of a patient's health condition.

These and other features and advantages of the disclosed system for measuring of cardiac blood flow balance parameter reside in the construction of parts and the combination thereof, the mode of operation and use, as will become more apparent from the following description, reference being made to the accompanying drawings that form a part of this specification wherein like reference characters designate corresponding parts in the several views. The embodiments and features thereof are described and illustrated in conjunction with systems, tools and methods which are meant to exemplify and to illustrate, not being limiting in scope.

BRIEF DESCRIPTION OF THE SEVERAL VIEWS OF THE DRAWING

FIGS. 7(a) and 7(b) are useful in explaining an embodiment of the invention on how to determine a cardiac auto-regulation rate and a respiratory rate determined from the cyclic variability of the balance parameter, computed for each cardiac cycle, and over a long term series of cardiac pulses;

FIG. 9 is a flow chart of an exemplary embodiment of the method for estimating aortic pulse waveform (AOP), defined by blood pressure, blood flow rate, or blood constituent concentration, based upon the estimated full aortic pulse and aortic arterio-venous pulse;

FIG. 14 is a flow chart of an exemplary embodiment of novel application of system identification methods for calculating the oximetry transfer function relationship between the red-light and infra-red plethysmograph waveforms of the full arterial pulses for arterial saturation, or the arterio-venous pulses for venous saturation.

DETAILED DESCRIPTION OF THE INVENTION

Figure 1:
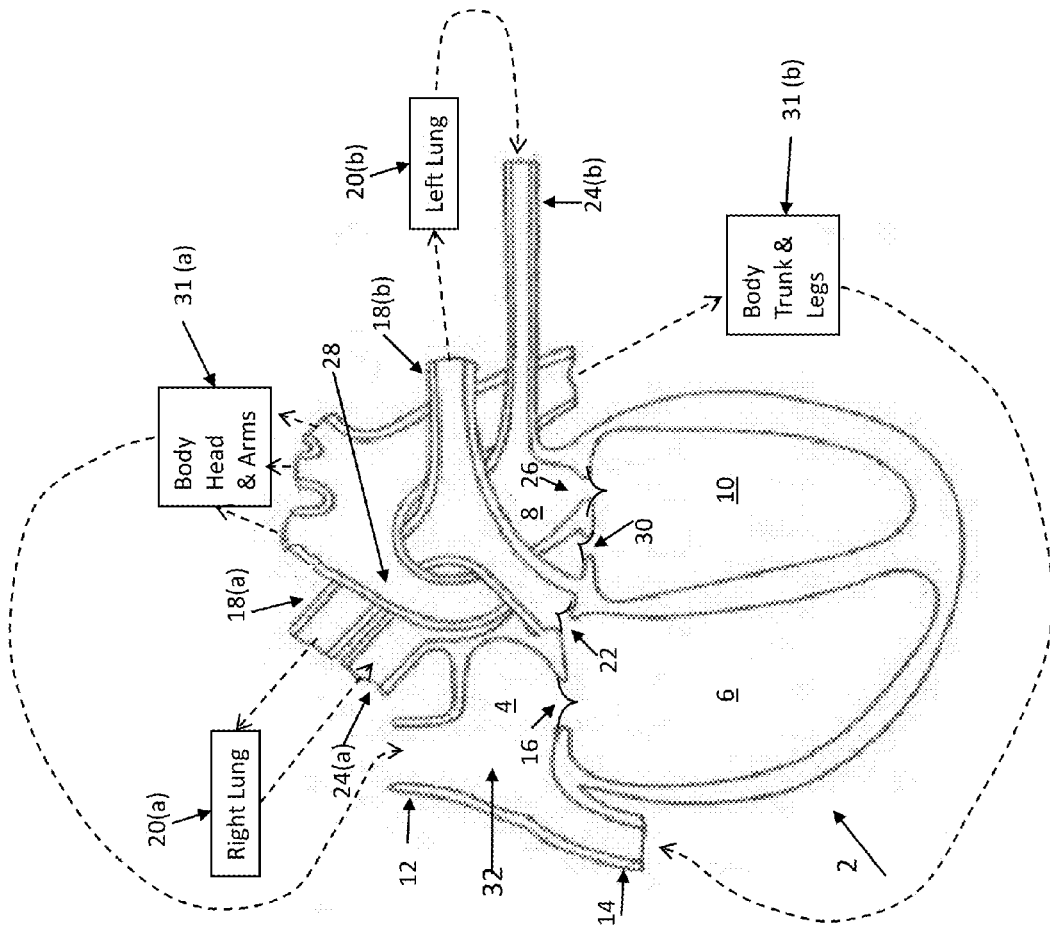
FIG. 1 is a simplified diagram of a patient's cardiovascular system, useful in explaining the blood flow through the heart and labeled "Prior Art"

Before explaining the disclosed embodiments in detail, it is to be distinctly understood at the outset that the present invention shown in the drawings and predominantly described in detail in association with a system for measuring of cardiac blood flow balance parameter is not intended to serve as a limitation upon the scope or teachings thereof, but is to be considered merely for the purpose of convenience of illustration of one example of its application. In particular, the present invention may be applied to any other suitable physiological monitoring systems, such as oximetry systems, ECG systems, and any other suitable for monitoring of a patient's liver, heart, lungs, brain, kidneys and other organs of the body.

Historically, the dicrotic notch was thought to represent a reflection of a fast pressure pulse that is generated when the aortic valve opens above its cracking pressure, and blood pressure reflecting backward from the arterial side back toward the aorta. When this delayed and damped pressure component of the pulse wave overlaps with the original pressure wave component, then this would result in the combined components creating the elevation called the Dicrotic Notch. However, this was later largely dismissed and replaced by the valve recoil effect theory. The valve recoil effect theory hypothesized that the Dicrotic Notch was the result of the valve recoil after its passive closure due to pressure drop in the start of the ventricular diastole phase. The valve recoil was believed to cause an elevation of the pressure post the initial decrease in pressure levels.

These theories however fail to explain why in some cases the Dicrotic Notch was completely missing in some patients, and in some other patients two dicrotic notches would appear. The fact that the Dicrotic Notch was not consistently seen in all subjects is another indication that this feature could not be entirely attributed to valve closure alone. The simultaneity of the valve closure event with the drop in pressure at the aorta and such event creating a change in the rate of reduction of blood pressure represented in the occurrence of the Dicrotic Notch has lead to the false presumption that the Dicrotic Notch was formed due to that valve closure event alone. The inventor believes that the circulatory cycle must be analyzed completely to consider interdependencies between the arterial and venous side in terms of blood flow continuity and timing effects.

It has been observed by the inventor that the atrial diastolic blood flow demand on venous blood has an interaction effect on the ventricular systolic arterial supply of blood such that this interaction affects the blood flow and subsequently blood pressure. Such interaction and timing characteristics between the ventricular supply and atrial demand of blood is what primarily defines the dicrotic notch feature of the aortic and arterial pulse. When ventricles start systolic contraction to eject (supply) blood, the atria start diastolic expansion to dilate to fill with (demand) blood, however, the atrial dilation extends longer in duration to also overlap with ventricular diastolic expansion. During this phase and in the absence of further blood supply the level of steep decline of the pressure is due to atrial diastolic blood flow demand, which starts from demand zero level reaches a maximum demand peak (i.e. supply trough) and then reduces to demand zero level. When atrial diastolic blood flow demand ends, due to atrial systolic phase beginning, then the decay rate of the arterial side supply pressure returns to its natural decay rate due to ventricular supply pulse pressure reduction alone at its natural decay rate. As the timing of this interaction and the level of supply and demand vary with patient's age or health state, there is sometimes observed the disappearance of the Dicrotic Notch or in other conditions the appearance of two Dicrotic Notches. This blood demand and supply interaction effect is realized across all the capillary interconnections between the venous vascular system and the arterial vascular system, and accumulatively the effect becomes stronger and more easily observed at larger arteries, especially at the aorta and pulmonary main arteries.

As was previously discussed, the pulse pressure at the aorta and other arterial peripheral branches exhibit "a forced" or "positively acted upon" loss of pressure that is subsequently followed by a rise in pressure, when this effect ends, resulting in the Dicrotic Notch. This is the primary effect creating the Dicrotic Notch. In other words, the two events (i.e blood pressure drop followed by rise) create the feature of the Dicrotic Notch. The rise in the pressure post the valve's passive closure can not be fully attributed to the valve's recoil post the closure event alone. When the valve's recoil occurs, it represents a substantially smaller secondary pressure perturbation than is often observed in the aortic valve's pressure wave about the Dicrotic Notch defined by the primary effect.

The atrial diastolic blood flow demand (i.e. venous side "pull") on the blood flow overlaps simultaneously with the ventricular systolic supply (i.e. arterial side push pressure) of the blood flow, during which the supply overwhelms the demand of blood and the pressure rises. The atrial diastolic blood flow demand then further overlaps with ventricular diastolic phase, which stops the blood supply due to heart valve closing effect, and allows the arterial pressure pulse to decay on its own natural decay rate. However, because of the continuous interaction with the atrial diastolic blood flow demand, which becomes the overwhelming dominant factor that reduces the blood pressure more rapidly at a forced decay rate that is steeper than the natural decay rate. This continues until the atrial systolic event start point, at which point the demand stops and the arterial decay rate returns to the natural decay rate. This interaction effects between demand and supply is substantially primarily responsible for the presence of the Dicrotic Notch. Such interaction profile is also varied or is affected by the blood viscosity or coagulation time, and can be used to estimate blood coagulation or coagulation variation. The venous side demand for blood flow overlapping with ventricular supply forces an increased blood flow through the capillaries greater than the rate it normally would occur at due to the arterial supply alone. It also lowers the realized pressure at the capillaries from the pressure levels that would be realized to accomplish the same flow rates due to arterial supply alone. This increased flow rate and at reduced pressure levels enhances the ability of blood cells to flow through the capillary bed more easily. In other words, the atrial diastolic blood flow demand assists the ventricular systolic blood flow supply in flowing the blood through the capillaries. The arterial pressure is affected by the presence or absence or interaction timing of the ventricular supply and atrial demand. The arterial supply pressure is lowered in the presence of the atrial (venous-side) demand pressure pulse. This venous side demand represented by the atrial diastolic blood flow demand pulse results in a reduction in the pressure on the arterial side at a faster rate (forced decay rate) than normal as compared to the case where the venous demand pulse was not present. Increased flow rate (due to venous side demand) also reduces the observed concentration at a fixed measurement point (per unit time) of blood constituents, such as oxygen content, which also results in the Dicrotic Notch being observed using optical plethysmography, for example. Similarly, blood flow rate sensors also depict the dicrotic notch feature due to blood flow acceleration in the presence of atrial demand and the interaction of ventricular supply as discussed previously.

As defined herein, the term "arterio-venous pulse" or (AV pulse) refers to the portion of the arterial pulse (representing blood pressure or flow or constituent concentration) that depicts level reduction due to the atrial diastolic blood flow demand for blood (from the venous side), and the arterio-venous pulse is therefore measured on the arterial side and not the venous side. When the arterio-venous pulse demand or "pull" reaches its maximum, the arterial pulse supply or "push" reduces (dips) to a low level presenting the valley of the Dicrotic Notch, this forced decay rate of the arterial pulse pressure or flow is restored back to its natural (unforced) decay rate once the arterio-venous pulse is completed representing the end of venous demand and the remaining reduction rate of the arterial pulse pressure or flow occurs at its normal decay rate. The subsequent cessation or stopping of venous side demand for blood flow results in the arterial pressure increasing back to what it would have been normally at (unforced natural decay rate) due to reduced flow in the arterial side. The Dicrotic Notch event itself is a representation of the arterio-venous pulse occurrence. The arterio-venous pulse demand "pull" accelerates the flow of blood by assisting the arterial pulse supply "push".

Venous side pulsations simultaneously add a blood flow component (i.e. increase blood flow) due to its demand for blood, and force the blood to flow faster. The presence of the arterio-venous demand pulse reduces the overall pressure to flow the blood through the capillary channels from levels required to achieve the same flow rates in the absence of the arterio-venous demand pulse. This venous pulsation (blood flow pull or demand) is therefore responsible (primarily) for the creation of the arterial side Dicrotic Notch. Aortic valve recoil has a similar but smaller (secondary) effect on the aortic pressure and arterial pressure. Those two factors (venous demand, and aortic valve recoil) forming the dicrotic notch are discernible. The difference in the effects of the aortic valve recoil versus the venous side demand on the dicrotic notch can become more obvious or separable in the presence of cardiac abnormalities causing atrial filling timing to be not synchronized with ventricular ejection. In these cases, multiple notches can be observed along the dicrotic limb of the pressure wave.

Valve characteristics do not change significantly from heart beat cycle to cycle, but the venous side demand (due to atrial filling) is variable from heart beat cycle to cycle. Therefore, the variations in the arterio-venous pulse across heart cycle-to-cycle can be safely attributed to variations in venous side demand and arterial side supply. Because pressure measurements are used to quantify the arterio-venous pulse and pressure is measured on the arterial side, the area under the curve, by integration over the cardiac cycle, for the arterio-venous pulse is expected to be smaller than that for the arterial pulse itself as the capillary bed small channels exist between the arterial and the venous sides. On the other hand, if flow rate were measured on the arterial side, then the flow out of the arterial side must substantially equal the flow into the venous side, less a small component of fluid potentially transferred in/out of the tissue.

Therefore, an arterio-venous pulse measured from a blood flow waveform (or equivalent indirect methods such as blood constituent concentration variation related to flow) that is detected at the arterial side is expected to have an area under the curve that is substantially equivalent to the area under the curve for the venous flow waveform.

As a result of the foregoing discussion, it can be seen that the fundamental basis of the present invention is founded upon the development of new and novel theory for explaining the occurrence of the Dicrotic Notch. The present invention describes novel measures and physiologic parameters that are used as clinical indicators of cardiovascular and pulmonary performance and health status from the analysis of the pulse wave and its features, including the Dicrotic Notch. Furthermore, this invention describes methods for measurement of such novel parameters via a variety of sensory devices and algorithms or processing steps. In addition, this invention describes several utility applications for use of the derived novel indicator into clinical applications.

Figure 2:
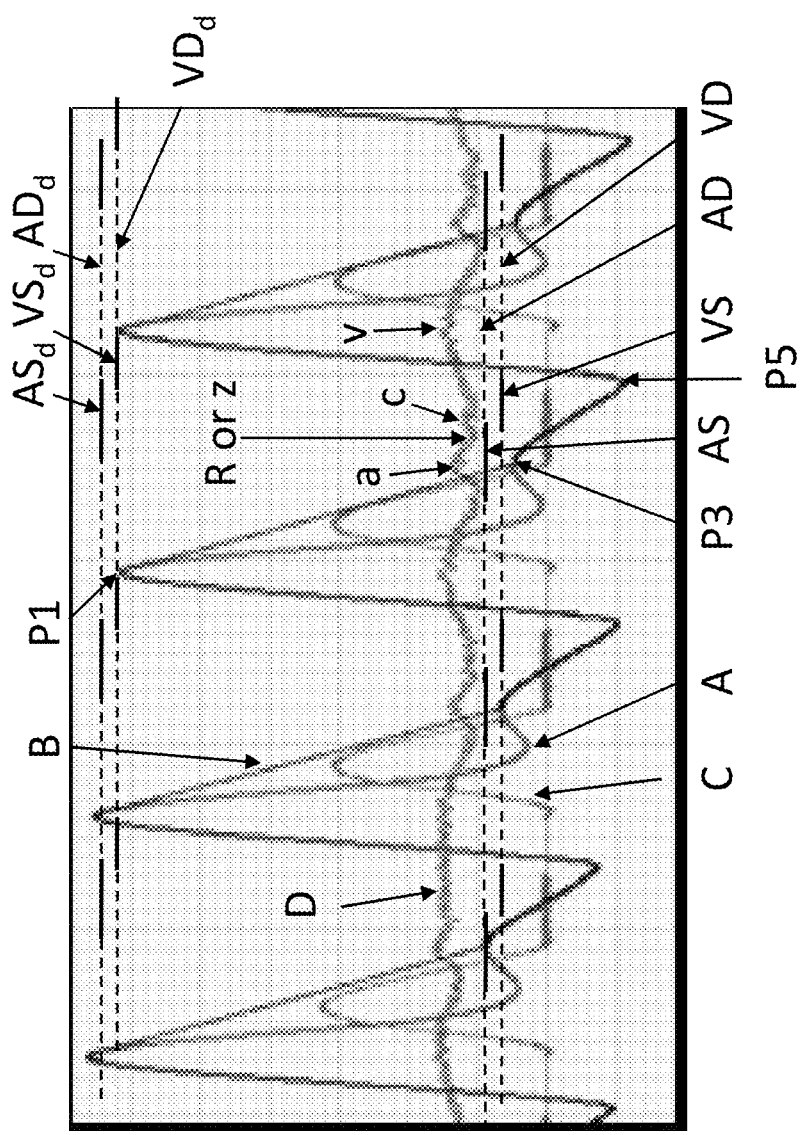
FIG. 2 depicts the various waveforms of a measured arterial pulse signal, a derived full arterial pulse signal, and a calculated arterio-venous pulse signal. It also depicts the simultaneously measured central venous pulse, and the systolic and diastolic phases of the atria and ventricles, as well as the delayed systolic and diastolic phases of the atria and ventricles as measured at the radial artery.

Referring now in detail to the various views of the drawings, there is illustrated in FIG. 2 a plurality of timing waveforms which are useful in explaining the present invention. The waveform A is the measured arterial pulse signal in a normal, healthy patient. The waveform B is the estimated full arterial pulse (FAP) signal representing the arterial pulse in the hypothetical absence of venous (atrial) demand. The estimated full arterial pulse (FAP) signal is based on a linear line interpolation between the primary peak and the secondary peak of the arterial pulse signal A. The waveform C is the derived or calculated arterio-venous pulse (AV) signal obtained by subtracting the observed or measured arterial pulse signal A from the full arterial pulse signal B. The waveform D is the central venous pressure (CVP) waveform. A delay (D1) between features in the central venous waveform and the radial artery waveform will be present and substantially equivalent to the delay between the aortic waveform and the radial artery waveform (D2), because of equivalent vascular lengths. This delay can be measured between the start of ventricular systole and the start of the cycle of increasing arterial pressure in the radial artery. Ventricular systole begins substantially synchronously with the R event of the QRS complex of the electrocardiogram (ECG) or electrogram (EGM) waveform. This R event is also synchronous with the point z of the central venous waveform D.

Other features of central venous waveform D are indicated as known in the art a-wave, c-wave, v-wave. Indicated on the FIG. 2 is the period of the following phases: atrial diastole AD, atrial systole AS, ventricular diastole VD, and ventricular systole VS. It is important to note that the depicted indication of systolic and diastolic phases is from a volumetric perspective and not from a pressure perspective. The difference being the iso-volemic periods. Also indicated is the delayed period of each of these phases when shifted in time by the previously indicated delay D1, and are indicated as follows: delayed atrial diastole ADd, delayed atrial systole ASd, delayed ventricular diastole VDd, and delayed ventricular systole VSd.

We notice that there is small overlap between (AS and VS) until ventricular valve open, however, there is a larger overlap between (AD and VS), (AS and VD), and (AD and VD). Similarly, there is small overlap between the delayed version of these phases (ASd and VSd) however, there is a larger overlap between (ADd and VSd), (ASd and VDd), and (ADd and VDd).

We note that in the interaction phase of (VSd and ADd) the ventricular supply overwhelms atrial demand and the pressure rises until the end of VSd, at which point the radial artery pressure reaches its maximum systolic value. Then the following phase is the interaction of VDd and ADd, however ventricular demand is blocked by the presence of valves, and the remaining effect on the radial pressure is the delayed atrial diastolic ADd demand. The pressure waveform depicts a natural slope of pressure decay once the pulse moves past the sensor, however, because of the contribution of the delayed atrial diastolic ADd demand, the radial pressure is forced to decay at a higher rate, until the next phase of interaction begins. Then the following phase is the interaction of VDd and ASd where atrial demand ends and the only remaining element is the natural decay rate of pressure, starting at the peak post the dicrotic notch. This natural rate of decay continues until the cycle restarts again with the interaction of the VSd and ADd. The period during the phase of interaction between VDd and ADd is the period of arterio-venous pulse waveform C, when atrial diastolic blood flow demand effect forces the slope of decay of the radial pressure to be more negative than the natural rate of pulse decay during the ventricular diastolic phase as indicated during the interaction of the phases VDd and ASd.

Measurements obtained at the central venous or pulmonary vein are generally low pressure about 8-12 mmHg but are higher power and higher in signal to noise ratio than those obtained at smaller veins. The central venous pulse is also significantly modulated by the respiratory cycle.

While it is obvious to the reader that the calculation of the balance parameter can be performed either from the arterial or venous measurements, and yielding equivalent results of balance parameter detection and trending, the remaining discussion herein will focus on arterial side measurements because of their higher measurement power and resolution, and easier interpretation of the full arterial pulse and the arterio-venous pulse relative to equivalent information from the central venous pulse.

The Dicrotic Notch is present in the waveform A of the arterial pulse signal. The Dicrotic Notch is defined by a characteristic valley which resides between the peak (point 1) of the arterio-venous pulse (also the beginning of the diastolic phase of the ventricle), which is also followed by a secondary peak (point 3) which also marks the end of the arterio-venous pulse.

In the hypothetical absence of atrial (venous side) demand for blood flow and if the arterial blood flow was solely due to ventricular supply, the decrease from the peak (point P1) of the arterial pulse wave A (representing blood pressure pulse or blood flow pulse) is modeled and presumed to be substantially linear over time, for simplification, until it reaches the start of the settling phase. The settling phase of the pulse wave A is defined to start at the secondary peak (point P3) after the Dicrotic Notch valley, which also indicates the end of the arterio-venous pulse and the secondary valley (point P5) of the pulse wave which defines its end (end of the diastolic phase) and the beginning of a new pulse wave (start of the systolic phase).

The delays between the CVP waveform D and the arterio-venous waveform C observed at the radial artery are substantially equivalent to the delays between the aortic pressure and the radial pressure. It will also be noted of the symmetry in the shape of the AV waveform C obtained by subtracting the arterial pulse waveform A from the FAP waveform B.

Figure 3:
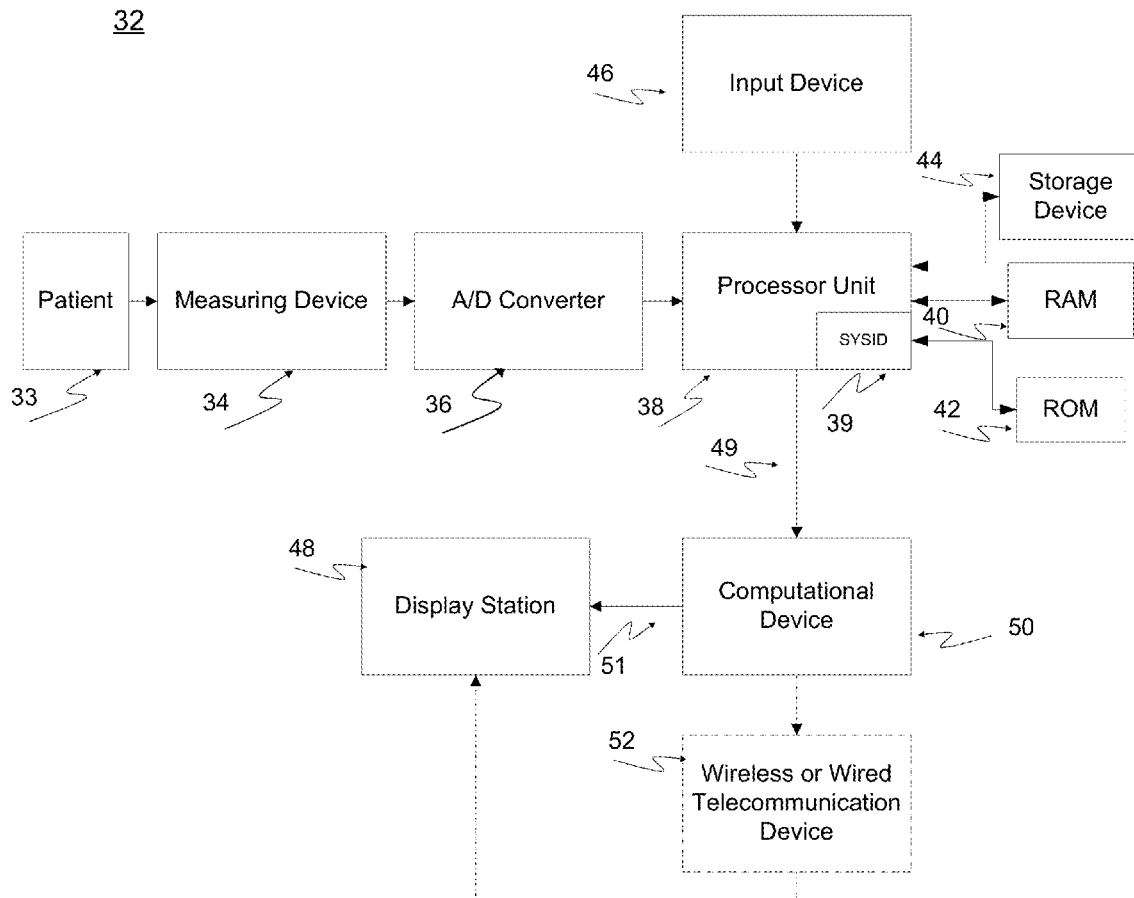
FIG. 3 is schematic block diagram of a system for producing a balance parameter and related information, constructed in accordance with the principles of the present invention.

In FIG. 3, there is shown a schematic block diagram of a system 32 for producing a balance parameter for use in one application, constructed in accordance with the principles of the present invention. The system 32 includes a sensing device or transducer 34, an A/D converter 36, a processor unit 38, a RAM 40, a ROM 42, and a storage device 44. The sensing device 34 is preferably a non-invasive arterial blood pressure or blood flow waveform measurement device operatively connected to a patient 33 for generating an arterial pulse signal. This arterial pulse signal is similar to waveform A in FIG. 2 and is fed as an input to the processor unit 38 via the A/D converter 36.

Further, the system 32 of the present invention includes a user input device 46 for inputting information to the processor unit, such as a keyboard or input terminal and a display station 48 for displaying useful information. The storage device can be any computer-readable media capable of storing information that can be interpreted by the processor unit, such as a hard disc, floppy disc, or other digital storage apparatus.

The sampling rate of the A/D converter 36 is set to at least two times according to the Nyquist criteria, but is preferably set to five times or higher than the highest frequency component of interest in the pulse waveform of arterial blood pressure, or blood flow signal, or blood constituent concentration so as to satisfactory capture the same. The A/D converter is used to digitized the analog arterial blood pressure or blood flow, or blood constituent concentration waveform signal generated by the sensing device. Alternatively, the processor unit could obtain the blood pressure or blood flow, or blood constituent concentration measurements in digital form directly from the sensing device so as to avoid the need of the A/D converter.

The sensing device 34 is preferably a non-invasive blood pressure, or blood flow, or blood constituent concentration waveform measurement device. A non-invasive blood pressure sensor such as a finger-cuff transducer unit using a counter pulsation technique in which the waveform is detected by balancing the air pressure in the finger cuff with the blood pressure in the patient's finger. A finger-cuff transducer unit of this type is commercially available from Ohmeda Monitoring Systems of Englewood, Colo. Also, tonometric blood pressure methods that press on the radial artery against the bone structure may be used to perform blood pressure measurements. A tonometric blood pressure of this type is the Vasotrac which is commercially available from Medwave. However, there exist many other prior art sensor types that can be used to measure either arterial and venous pulse pressure waveforms.

For blood flow measurements, this can be achieved by using non-invasive acoustic ultrasonic doppler frequency effect sensors, or using an electromagnetic wave (such as light or RF), or by directly using motion sensors, accelerometers, or using coriolis sensors, or by thermodilution methods, or dilution of concentration of a chemical such as lithium or dye or a radioactive material, or dilution of concentration of a blood constituent or component, or using differential pressure sensors measurements (for example Venturi flow sensing or orifice pinhole type sensors). Similarly, pulse flow can also be assessed using the dilution or concentration of a radiotracer chemical element such as those used in nuclear medicine, fluoroscopy, or in magnetic resonance functional imaging.

For blood constituent concentration measurements, this can be achieved by using a noninvasive optical pulse oximeter or using electrochemical sensors that have specificity and sensitivity to the target chemical analyte or blood constituent component.

For blood pressure measurements, this can be obtain using many sensor types including resistive or capacitive or inductive measurement elements, and any of the following broad categorizations of general types of sensing technologies including:

Invasive method include placement of a catheter to obtain pressure measurements consisting of:
  Using implantable sensors that reside in a vascular branch or in a cardiac chamber or body organ.
  Using catheter mounted pressure sensors, or via catheter fluidic channel pressure measurement over the extended catheter using a pressure sensor that is either built into the catheter or external to it.
Minimally invasive methods include access to the artery or vein channel using a cannula and using a pressure sensor connected to the cannula channel to measure the vascular artery or vein pressure.

Non-invasive methods including:
Tonometric pressure pulse sensing methods
Optical pulse sensing methods
RF pulse sensing methods
Acoustic pulse sensing methods such as those relating the Doppler frequency shift with the flow rate change.
Vibration pulse sensing methods such as placement of a accelerometer or force sensor in proximity to the vascular channel where pulse waveform or pulse velocity is intended to be measured.
Blood magneto-acoustic methods which use measurement of an electric current that is resultant from ion movement in a magnetic field.

Blood temperature dynamic variation can also be representative of the dynamics of the blood pulse when measured at a frequency high enough that is representative (at least twice as high based upon the Nyquist criteria, but preferably five times as high) of the dynamics of variations of the pulse. This is due to the thermal dilution gradient of the blood as it is accelerated past the sensor. This measurement can be also obtained more easily non-invasively, for example, using infrared sensors.

Blood constituents dynamic variations are also indicative of the pulsatile flow when measured at a frequency high enough that is representative (at least twice as high based upon the Nyquist criteria, but preferably five times as high) of the dynamics of variations of the pulse. Such dynamics variations are indicative of the arterial pulse and are evident in the measurement of blood plethysmography.

Optical measurement can also be obtained for measurement of blood oxygen content or blood carbon-dioxide content. Optical measurements can also be obtained from measurement of blood constituents such as blood glucose. Because optical blood constituent analysis can be done very fast and without residual historic measurement effects on the sensor, they are more suited for real time measurements throughout each cardiac cycle than chemical sensors with large response time constant and settling times.

The monitoring of the cardiac balance parameter in the present invention can be accomplished using pulsations measured from any artery, including, but not limited to, aortic, carotid, pulmonary, femoral, radial, renal, and hepatic arteries. Similarly, the monitoring of the cardiac balance parameter can be accomplished using pulsations measured from any vein including, but not limited to, central venous, superior vena cava, inferior vena cava, jugular, pulmonary, femoral, radial, renal, and hepatic veins. However, the signal power measured at a vein is much smaller than an artery. Nonetheless, the same primary components related to arterial supply and venous demand can be identified from venous measurements per cardiac cycle of any of blood pressure, blood flow, or blood constituent concentration and can be used for quantifying the balance parameter.

A balance parameter determined by measurements from the central venous, central venous branches, the aorta, or aortic arterial branch is called Left Right Balance (LRB), and a balance parameter determined from the pulmonary vein, pulmonary vein branches, pulmonary artery, or pulmonary arterial branches is called Right Left Balance (RLB).

In addition, the monitoring of the cardiac balance using a pulse waveform measured from any artery or vein can be accomplished with any of the aforementioned sensor types and sensory methods of measurement including invasive, minimally invasive, or noninvasive blood pulse monitoring, and including pulse waveforms that are indicative of blood pressure, blood flow rate, or blood constituent or components dynamic variation over time.

Under the control of a software program stored in the ROM 42 or the storage device 44, the processor unit 38 will derive the full arterial pulse (FAP) signal, as shown in the waveform B in FIG. 2, based upon the observed or measured arterial pulse signal A. Then, the processor unit 38 will calculate the arterio-venous (AV) pulse signal, as shown in the waveform C of FIG. 2, by subtracting the measured arterial pulse signal from the FAP signal. Finally, the processor unit will determine a balance parameter at its output 49 of the present invention by calculating the ratio of the area under the curve of the AV pulse signal, measured by integration over the cardiac cycle, to the FAP signal, measured by integration over the same cardiac cycle. This balance parameter 49 is sent by the processor unit to a computational device 50 for generating a set of physiological parameters on its output 51 which are useful to indicate a clinical assessment of the patient's health condition.

The display station 48 receives the set of physiological parameters 51 from the computational device 50 for providing visual and audio monitoring of the patient's health condition and for alerting medical personnel of changes in the patient's health condition. As an option, a wired or wireless telecommunication system 52 shown in phantom may be coupled to receive the set of physiological parameters from the computational device 50 and for transmitting wirelessly the set of physiological parameters to the display station 48, which can be located at a remote site away from the patient.

In the embodiment shown, the processor unit 38 is comprised of a general-purpose microprocessor which is adapted to execute software consisting of an operating system and one or more applications, as part of performing the functions described hereinbelow. Further, each of the various blocks illustrated in FIG. 3 is merely exemplary in nature and is intended to show one implementation of the system for providing the balance parameter using the arterial pulse signal and should not be construed as limiting. Indeed, the different embodiments may have widely varying software programs, data structures, applications, processes, and the like. Therefore, the various functions of each block may in actual practice be combined, distributed, or otherwise arranged in any suitable fashion.

The processor unit 38 includes a System ID Processing Device 39 for establishing a transfer function relationship between FAP pulses of any artery in the left heart vasculature (as an input or inputs to the model) and the aortic artery main pulse which represents the primary source of such a pulse (as an output to the model). Similarly, the System ID Processing Device 39 can be used to establish a transfer function relationship between full arterial pulses (FAP) or arterio-venous (AV) pulses of any two arteries, defined in forward or backward input/output transfer function modeling steps. For example between the aorta and any of its arterial branches, or between the pulmonary artery and any of its arterial branches. Such transfer function relationships relate the pulses from a plurality of locations as input or output in order to use a more readily observable signal to estimate a more difficult to observe signal. For example, used in the right heart vasculature tree (as an input or inputs to the model) and the pulmonary artery main pulse as a primary source of such a pulse (as an output to the model). Preferably, linear state-space models can be used for establishing such transfer function relationship.

The aortic or pulmonary artery full arterial pulse (FAP) can be used as the source (input) producing the (peripheral) full arterial pulses (output) in the arterial branches, or the reverse (or inverse) model can be used. Similarly, the aortic or pulmonary artery arterio-venous pulse can be used as the source (input) producing the (peripheral) arterio-venous pulses (output) in the arterial branches, or the reverse (or inverse) model can be used. Whereas the estimated output arterio-venous pulse can be subtracted from the estimated output full arterial pulse to produce the estimated observed arterial pulse.

Similarly, the System ID Processing Device 39 can be used to establish a transfer function relationship between FAP pulses of any artery and the arterio-venous (AV) pulse from that same pulse, representing a model of the balance parameter. Preferably, a simple ratio of the AV pulse to the FAP pulse, i.e. a linear relationship of the first order can be determined. Also, a more generalized linear model of any order identified using system identification methods, preferably state-space model, can be used to describe the balance parameter as a system relationship. Such a generalized model will capture the relative amplitude ratio and timing delay (phase shift) information between the AV and FAP signals. Optionally, in a second step, given the balance parameter, or a model of it, and the input FAP, then the output AV pulse can be estimated.

Selection of either inputs or outputs allows for estimation or prediction of an unknown output, given an identified model parameters and measured inputs. A MISO (multiple inputs single output) type model mapping the relationship between a plurality of peripheral artery pulses (inputs, more easily measured) into the main primary source aortic or pulmonary artery pulse (output, more difficult to measure) for that vasculature is a preferred embodiment for enhancing accuracy and enabling easier prediction of the central pressure at the main vessel. For a single peripheral pulse, a SISO (single in single output) model is preferably used. Once a model is identified and the coefficients are defined, then the model can be used with the plurality of input peripheral pulses to estimate or predict the primary source arterial pulse.

Such stated pulse(s) can be produced by a measurement from different types of sensors including measurement of blood pressure, blood flow rate, blood temperature, or blood constituent concentration, such as hemoglobin, or glucose, or oxygen, or carbon dioxide content. The same principles of model identification can be applied using either the raw measured pulses or the estimated FAP pulses (full arterial pulse composed of the raw measured pulse plus the arterio-venous pulse) using any of these types of measurements.

Such models relating peripheral arterial (radial, femoral, renal, etc.) measurements and central arterial (aortic or pulmonary artery) measurements which can be identified using system identification methods can be used for estimation of such unknown blood constituent concentrations at a primary (central or main) blood vessel using only the measured peripheral blood constituent concentration. Such model based estimation methodology can lead to more accurate systemic estimation/measurement of such constituent concentration and therefore enable better medication delivery titration. Such medication delivery titration is desired for control or regulatory compensation of the desired constituent, especially with closed-loop feedback control systems, of which model free adaptive control or model predictive controllers (MPC) are two preferred embodiments. Similarly, a linear system identification, preferably state-space model, can be applied across peripheral Full Arterial Pulses (FAPs) such that an estimation of an output peripheral FAP from another input peripheral FAP can be obtained.

While there are available many tools and system identification strategies, the preferred embodiments of the present invention utilizes a direct system identification which uses state-space methods, and preferably in a multiple input single output (MISO) or single input single output (SISO) configuration, as more fully discussed below. The state-space MISO or SISO system identification allows implementation of system identification methods to the application of cardiovascular and pulmonary physiologic parameter estimation, and in the further improvement of application of the Balance parameter as input to such models to yield enhanced estimations to those parameters as model outputs. This invention applies the science of system identification to the realization of a feasible cardiovascular and pulmonary physiologic parameter estimation.

Figure 4:
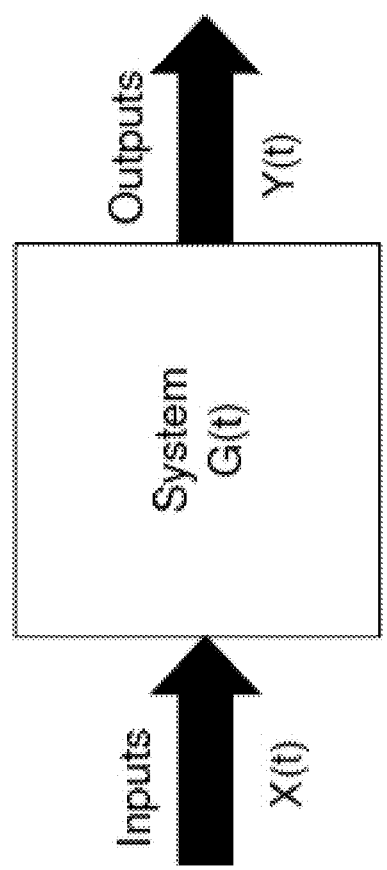
FIG. 4 is a system transfer function which illustrates the time domain and frequency domain relationships between the input and output time series.

In FIG. 4, there is depicted a system transfer function G(t) which illustrates the relationships in the time and frequency domains between the inputs X(t) and outputs Y(t). As can be seen, in the time domain the inputs X(t) are convoluted with the transfer function G(t) to produce the outputs Y(t). On the other hand, in the frequency domain the inputs X(f) are simply multiplied in order to obtain the outputs Y(f). Thus, the linear state-space model identification from frequency response function allows ease of adaptation of the system model using a change to its model order to optimize its approximation or estimation of the system outputs.

The state-space models (as described in reference 4, Linear Estimation, Kailath, Sayed, Hassibi. Prentice Hall, 2000, which is hereby incorporated by reference) are defined as $$x(k+1) = Ax(k) + Bu(k)$$

$$y(k) = Cx(k) + Du(k) + n(k)$$

Where u(k), y(k), and x(k) are time series of real numbers representing the input, output, and state variables, respectively, of the system, and n(k) is time series of real numbers representing the noise term which is assumed to be independent of the input sequence u(k). A, B, C, and D indicate the coefficients vectors. The state variables represent the unforced dynamics of the system model.

By using the Fourier transform on both sides of both equations of the state-space model, we obtain the following, where .sup. indicates superscript, and exp indicates the exponent:

$$(\exp^{jw}) X(w) = AX(w) + BU(w)$$

$$Y(w) = CY(w) + DU(w) + N(w)$$

Where w is the frequency term, j indicates an imaginary number, and Y(w), U(w), X(w), N(w) are the frequency transformed output, input, noise, and state variables. The variables A, B, C, D indicate the coefficients vectors. Where $$G(\exp^{jw}) = G(z) \text{ at } z = \exp^{jw} =$$

$$D + C((zI - A)^{-1})B \text{ at } z = \exp^{jw} \text{ and,}$$

$$Y(w) = G(\exp^{jw}) U(w) + N(w)$$

is the frequency response function (FRF) of the system. I represents the identity matrix and .sup.-I represents a matrix inverse.

It will be noted that many other conventional System Identification methods exist and can provide substantially equivalent implementations to the state-space methods preferred in the present invention. These include (a) linear system identification (SYSID) methods, (b) nonlinear system identification methods, and (c) blind system identification methods. The background of each is discussed in details with algorithms describing prior art implementation details of such methods. The methods described apply for SISO (single input single output), MISO (multiple input single output), SIMO (single input (stimulus) multiple outputs (responses)), and MIMO (multiple inputs (stimuli) multiple outputs (responses)) configurations. This instant invention can equivalently, without loss of generality, use any of the other system identification methods mentioned below, and in any configuration of the inputs and outputs mentioned previously.

For example, as described in the references 1 through 6 listed in the Appendix, which are incorporated herein by reference, which describe linear systems estimation and system identification methods, the linear SYSID parameteric and non-parameteric methods include:
AR
ARX
ARMA
ARMAX
Generalized Linear
Output Error
Box-Jones
Continuous transfer function
Discrete transfer function
Impulse realization
User defined model
Principal components subspace identification
Discrete frequency transfer function from frequency response function
Continuous frequency transfer function from frequency response function
Maximum likelihood methods The nonlinear SYSID methods include:
Neural Networks
Fuzzy Logic
Volterra Series
Weiner models (LMS, or recursive least square based)
Wavelets analysis
Nonlinear state-space models The blind system identification methods include:
Laguerre model based
Deconvolution methods The cardiovascular or pulmonary measured pulse waveform can refer to any of the following in continuous waveform or discrete values that are absolute or relative in value:
Blood pressure in any vascular location or cardiac chamber.
Blood flow rate in any vascular location.
Blood volume in any cardiac chamber.
Blood constituent concentration or chemical analyte concentration in any vascular location or cardiac chamber.

The system identification of the present invention can be either a SISO, if for example a single input channel was mapped to a single output channel, or, preferably, a MISO if the identified system was determined by mapping (or relating) multiple input channels (stimuli, measured cardiovascular or pulmonary parameters) into a single output channel (response, estimated cardiovascular or pulmonary parameter). Multiple inputs mapping provides greater informational content and therefore a better mapping accuracy to the output.

Alternatively, a MIMO configuration can be used where the input measured signals (measured cardiovascular or pulmonary parameters) are used to calculate multiple output responses (estimated cardiovascular or pulmonary parameters) in a single application of system identification methods rather than multiple applications of multiple subsystem identifications. Alternatively, a SIMO configuration can be applied where a single (measured cardiovascular or pulmonary parameter) is used as an input to determine system relationship with multiple outputs (estimated cardiovascular or pulmonary parameters).

Figure 5:
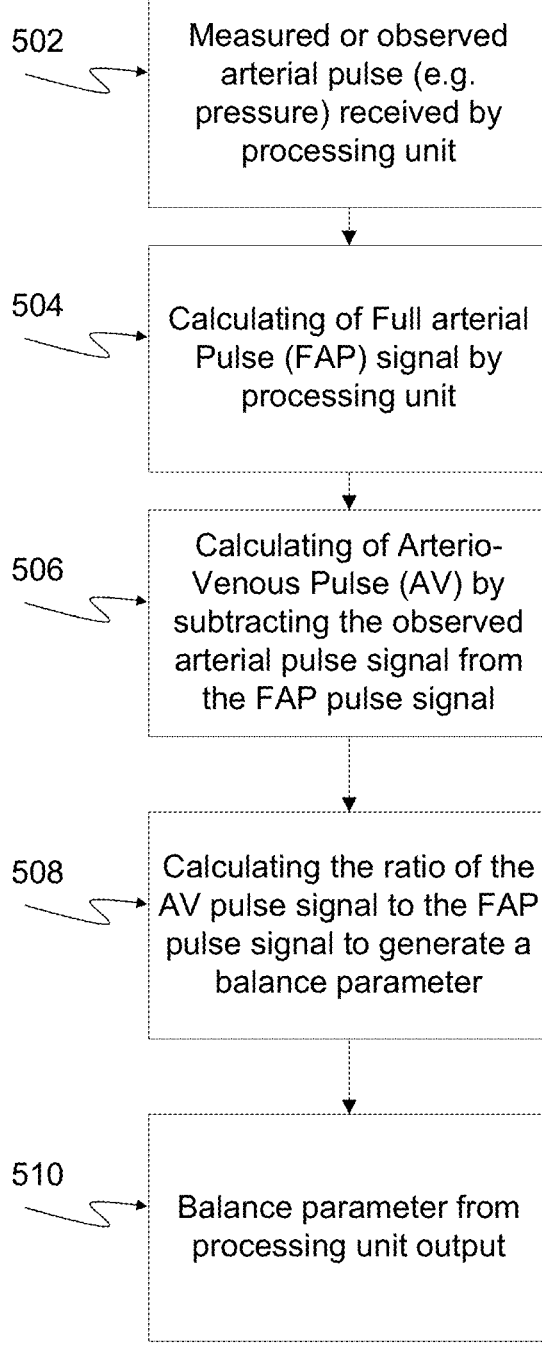
FIG. 5 is flow diagram of an exemplary embodiment of the software used by the microprocessor in FIG. 3 for generating the balance parameter and related information.

FIG. 5 is flow diagram of an exemplary embodiment of the software used by the microprocessor in FIG. 3 for generating the balance parameter. The process 500 is performed by the processing unit 38. Initially, at step 502 the measured or observed arterial pulse waveform signal A of FIG. 2 is generated by the sensing device 34 and is received by the processing unit 38. At step 504, the processing unit calculates or derives the full arterial pulse (FAP) waveform signal B of FIG. 2 based upon the observed or measured arterial pulse waveform signal A. Next, in step 506 the processing unit calculates the arterial-venous (AV) pulse waveform signal C of FIG. 2 by subtracting the arterial pulse waveform signal from the FAP waveform signal. Finally, at step 510 the balance parameter 49 at the output of the processing unit is calculated by the ratio of the area under the curve of the AV pulse waveform signal, measured by integration over the cardiac cycle, to the FAP waveform signal, measured by integration over the same cardiac cycle, in step 508. Whereas the DC offset can be either included in the integration, or normalized, or removed by subtraction.

Figure 6:
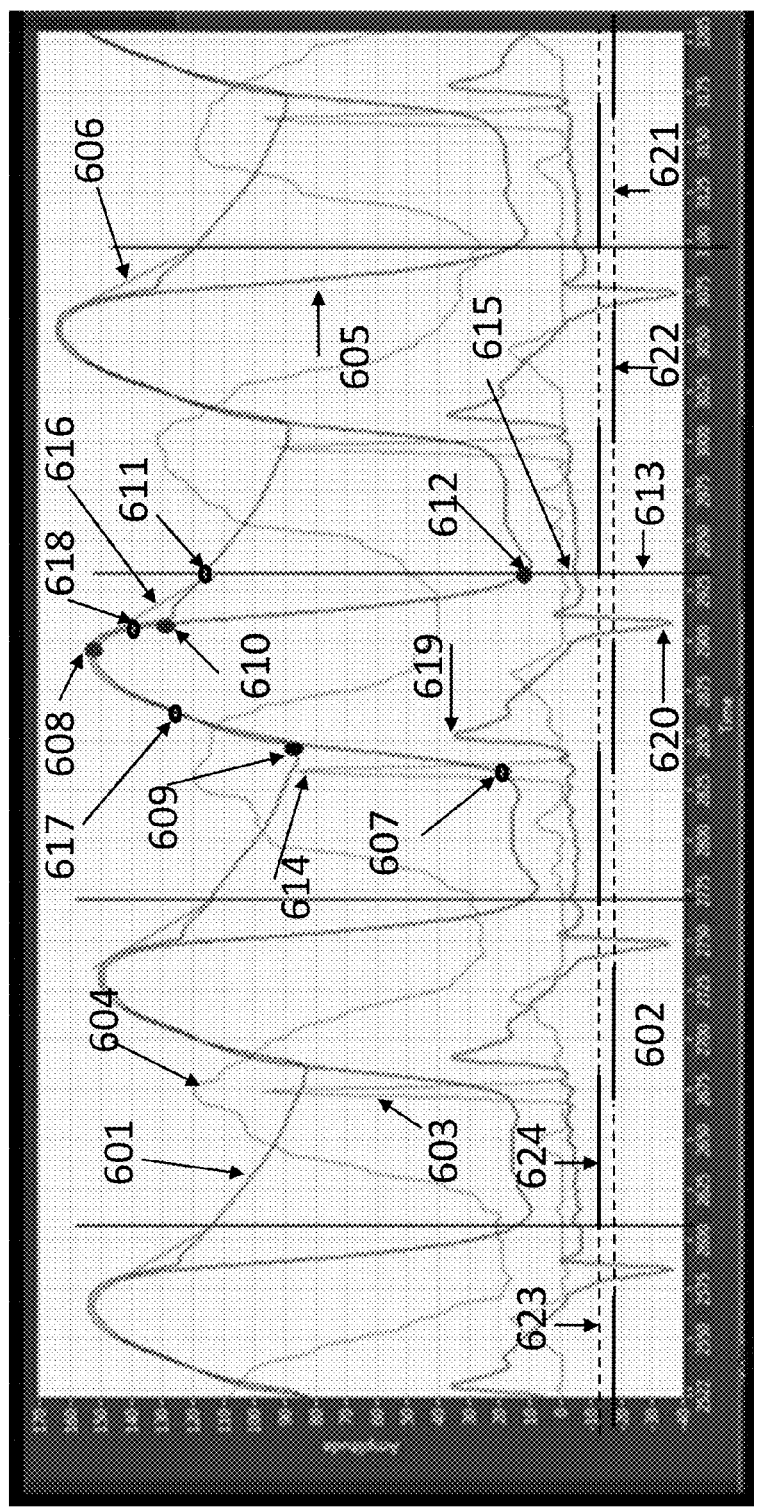
FIG. 6 are waveforms useful in explaining an embodiment of the invention on how cardiac volumetric and performance parameters can be determined using aortic pressure measurements allowing determination of the left ventricular pressure at certain key pressure points, which can be useful in mapping pressure information to volume information.

With attention directed to FIG. 6, there are shown a plurality of waveforms which are useful in explaining an embodiment of the present invention with respect to how certain key pressure points on the left ventricular pressure (LVP) or right ventricular pressure (RVP) signal can be determined based upon an aortic pressure or pulmonary artery measurement (or an estimate thereof). In particular, the key pressure points of interest include end-systolic pressure (PES), pre-diastole end-systolic pressure (PDPES), and end-diastolic pressure (PED). The timing timeline for atrial and ventricular systolic and diastolic phases are depicted to ease the interpretation of the full aortic pressure pulse, given the context of previous discussions in FIG. 2. It is important to note that the depicted indication of systolic and diastolic phases is from a volumetric perspective and not from a pressure perspective. The difference being the iso-volemic periods. The atrial diastolic phase is 623. The atrial systolic phase is 624. The ventricular diastolic phase is 621. The ventricular systolic phase is 622. Adopting a pressure based convention for systolic and diastolic phase definition simply modifies the start and end of the defined phases.

PED substantially represents the pressure point on the ventricular pressure signal occurring pre iso-volemic contraction prior to the systolic contraction of the heart volume and after the diastolic expansion phase end. The end-systolic pressure (PES) and the PDPES pressure however are two separate pressure points on the ventricular pressure signal. The PDPES is indicative of the ventricular pressure value post the isovolemic relaxation phase and prior to diastolic expansion. The PED is indicative of the ventricular pressure value post diastolic expansion and pre-isovolemic contraction phase. While PED detection is generally easily detectable from the waveform of the ventricular pressure signal directly, the PDPES pressure point is not detectable directly therefrom since it is often affected by active forces of chamber muscle compression changing its relative timing.

The atrial diastolic blood flow demand creating filling of the atria and during the overlapping phase with ventricular isovolemic relaxation (indicated as part of ventricular volumetric diastole) is what creates the arterio-venous pulse, which is, as described herein, detectable at the aorta. Therefore, the timing signature marking the end of diastole for the atria must be detectable in the aortic pressure at the end of the arterio-venous pulse. This same event can be used to mark the end of the isovolemic relaxation event for the ventricle, after the systolic contraction phase end, at which point such pressure value in the ventricle (PDPES) represents substantially the post iso-volemic relaxation which occurs prior to diastolic expansion of the ventricular volume.

As can be seen in FIG. 6, the first waveform 605 is the measured ventricular pressure signal. The second waveform 601 is the measured aortic pressure (AOP) signal. The third waveform 603 is the measured electrocardiogram (ECG) signal, but can be equivalently replaced by an electrogram (EGM) signal. The fourth waveform 604 is a representation of the volume of blood in the ventricle. Finally, the fifth waveform 602 is the first derivative of the aortic pressure (AOP) signal 601.

The first key pressure point is PED which is designated by the dot 607 on the ventricular pressure signal 605. The second key pressure point is PDPES which is designated by the dot 612 on the ventricular pressure signal 605. The third key pressure point is the maximum ventricular pressure which is designated by the dot 608 on the ventricular pressure signal 605. The fourth key pressure point is the point where ventricular pressure is equal to aortic pressure which is designated by the dot 609 located at a first intersection of the ventricular pressure signal 605 and the AOP signal 601. The fifth key pressure point is the point where the ventricular pressure signal separates from and is no longer equal to the AOP signal which is designated by the dot 610 located at a second intersection of the ventricular pressure signal 605 and the AOP signal 601.

Advantageously, the measurement of PDPES in this embodiment of the present invention is obtained from the measured waveform of the ventricular pressure signal 605 (or its estimate), and using event timing information derived from the waveform of the aortic pressure signal 601. The derivative 602 of the aortic pressure signal depicts a small peak indicated by the dot 615, at which point the ventricular chamber is at end systole, and the atrial chamber is at end diastole. At that event, the atrial diastolic blood flow demand ("pull effect") of blood interaction with the ventricular blood flow supply ("push effect") of blood reaches the phase end (end of arterio-venous pulse) where an aortic pressure first derivative 602 inflection point peak at that point indicates such event 615.

Therefore, the PDPES (the dot 612) from the ventricular pressure 605 can be measured (or estimated) at that event's timing, which is also indicated with an inflection point 615 in the first derivative 602 of the aortic pressure 601. It should be noted that the following observations can be made:

1. PED can also be preferably detected at the ventricular pressure point when the ECG or equivalently EGM waveform triggers its R event in the QRS wave complex. PED alternatively can be measured from the ventricular pressure waveform directly using its 1st derivative valley.
2. PES can be measured from the ventricular pressure waveform by finding the maximum value.
3. The valve open event (the dot 609) is detected preferably by the maximum peak 619 of the aortic pressure first derivative, or by the minimum valley of the aortic pressure, or by a peak of the first derivative of the ventricular pressure.
4. The valve close event (the dot 610) is detected preferably by the minimum valley 620 of the aortic pressure first derivative, or the valley of the aortic pressure at the dicrotic notch, or a valley of the first derivative of the ventricular pressure.
5. The duration of the ventricular iso-volemic contraction event spans the duration of the end of P wave to R event in the QRS complex. Alternatively, preferably, it can be defined as spanning the QRS complex event duration.
6. The duration of the ventricular iso-volemic relaxation event spans the duration of the electrical silence period of the heart.

The Balance parameter can be assessed from the aortic artery (or pulmonary artery) pulse signal using an estimation of the arterio-venous (AV) pulse signal, defined as the subtraction of the measured or observed arterial pulse from the full arterial pulse (FAP) signal at these two locations of the aorta or pulmonary artery. The aortic full arterial pulse (FAP_aortic) (or equivalently the pulmonary artery full arterial pulse FAP_pulmonary) is measured by extending a linear line 616 between the maximum pressure (peak-dot 608) of the aortic pressure signal 601 until the end of the dicrotic notch, at which point it is advantageously substantially synchronous in timing with the PDPES (the dot 612), which is detected from the aortic pressure signal (or its estimate) using a inflection peak (the dot 615) of the first derivative of the aortic pressure signal as indicated in the waveform 602 of FIG. 6.

Still referring to FIG. 6, the small peak 615 of the first derivative (waveform 602) of the aortic pressure signal 601 indicated at the vertical line 613, corresponds with the pre-diastole end systolic event (PDPES) which is indicated on the ventricular pressure waveform 605 with the dot 612 and on the aortic pressure waveform 601 with the dot 611. This PDPES event also corresponds with the ventricular volume being the smallest and is substantially coincident to the extended linear line 616 across the aortic pressure signal 601 used to define the FAP_aortic pulse 606. The vertical line 613 intersects the first derivative (waveform 602) of aortic pressure signal 601 at a inflection point 615.

Similarly, the end-diastolic event at which end-diastolic pressure (PED) is detected, defined by the ventricular pressure point post completion of the ventricular diastolic expansion, and prior to the onset of isovolemic contraction, is indicated as corresponding to the timing of the R-event 614 of the electrocardiogram (ECG) (or equivalently of an electrogram (EGM)) QRS-complex in the ECG (or equivalently EGM) waveform 603. The PED value on the ventricular pressure waveform 605 is indicated by the dot 607. The maximum ventricular pressure is also indicated on the waveform 605 by the dot 608, which is equivalently the maximum aortic pressure on the waveform 601. The dot 609 indicates the valve open pressure event, when both the ventricular pressure in the waveform 605 and the aortic pressure in the waveform 601 become equal. The dot 610 indicates the valve close pressure event, when the aortic pressure in the waveform 601 departs from the ventricular pressure in the waveform 605.

Figure 10A:
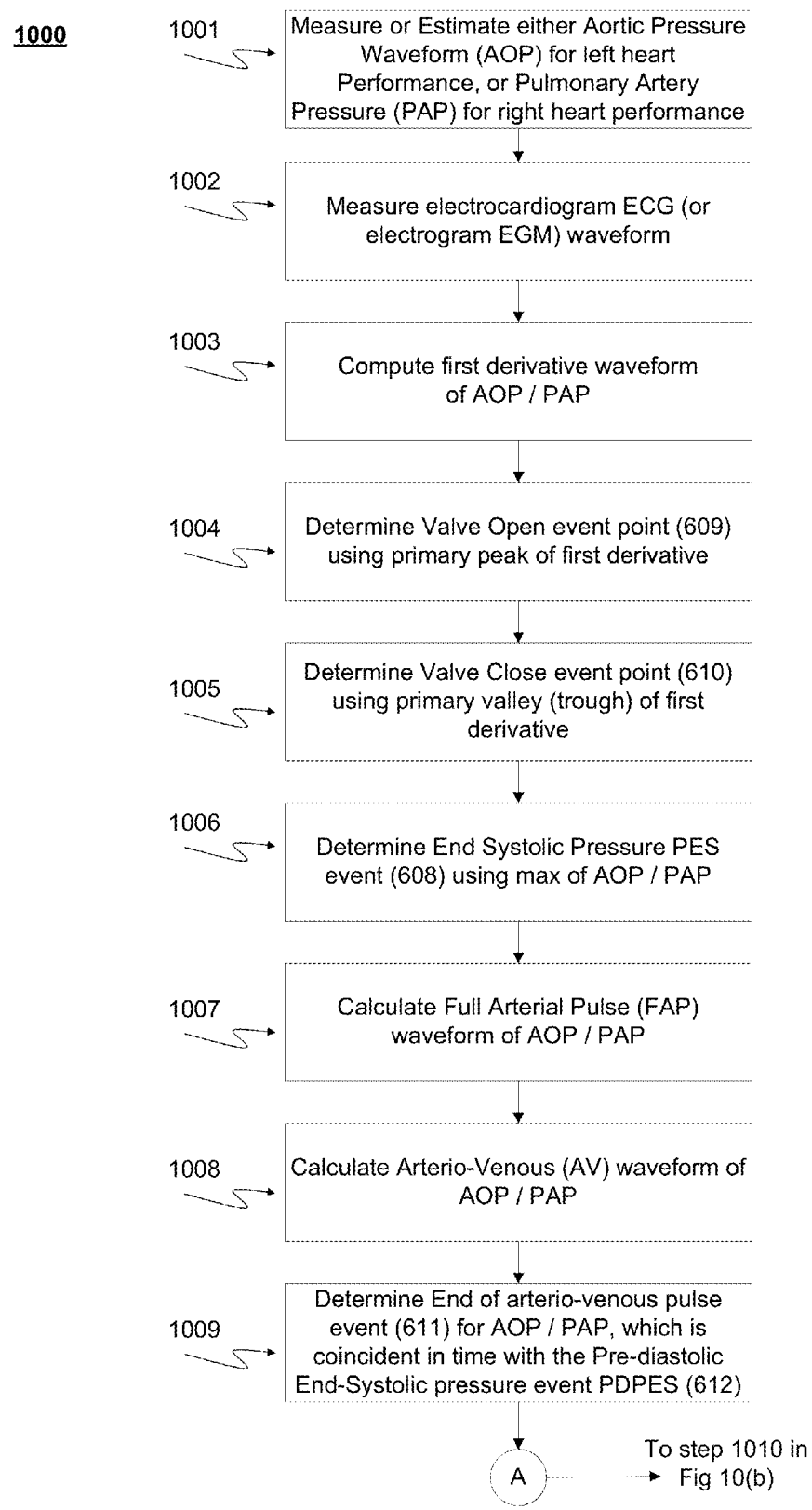
FIGS. 10(a) and 10(b) is a flow chart of an exemplary embodiment of the method of FIG. 6 used to determine ventricular pressure static points of end-diastolic pressure (PED), and pre-diastolic end-systolic pressure (PDPES) for use in computation of ventricular end-diastolic volume, end-systolic volume. It also describes the determination of PED and PDPES using aortic pressure alone without ventricular pressure information.
Figure 10B:
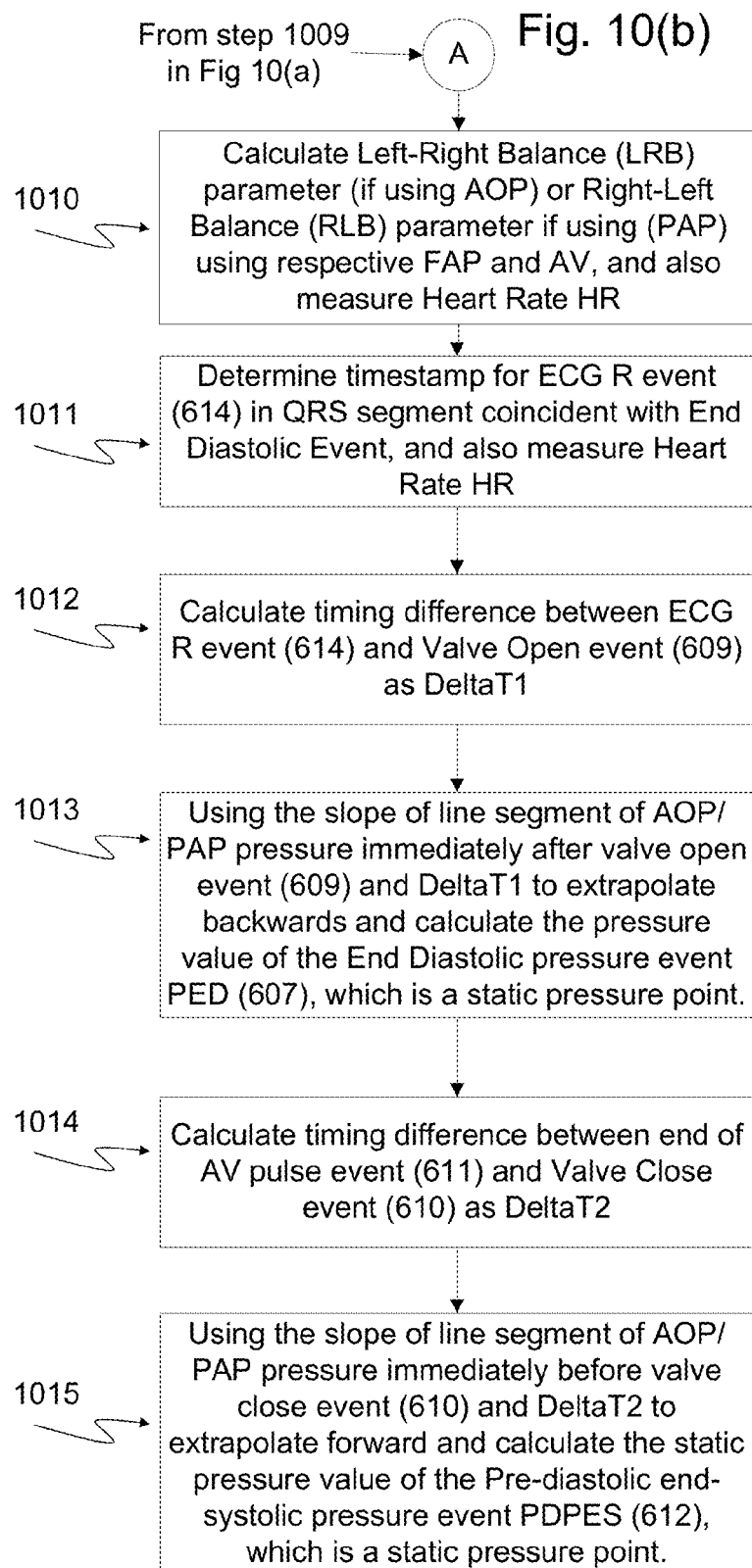

With attention directed to FIGS. 10(a) and 10(b) of the drawings, there are shown, when joined together, a flow chart 1000 of an exemplary embodiment of the unique method of the present invention in FIG. 6 used to determine the PED and the PDPES values on the ventricular pressure signal for assessing the cardiac ventricular volumes and other cardiac performance parameters. Initially, in step 1001 a measurement (or an estimate thereof) of either the aortic pressure (AOP) waveform for the left heart performance or the pulmonary artery pressure (PAP) for the right heart is obtained, which is similar to the waveform 601 shown in FIG. 6. A measurement of the electrocardiogram (ECG) (or electrogram (EGM)) waveform is obtained in step 1002, which is similar to the waveform 603 shown in FIG. 6. In step 1003, the first derivative waveform of the waveform obtained from step 1001 is computed, which is again similar to the waveform 602 depicted in FIG. 6. Next, in step 1004 the valve open event (the dot 609 in FIG. 6) is determined by using the maximum peak of the first derivative waveform obtained from the step 1003. Similarly, in step 1005 the valve close event (the dot 610 in FIG. 6) is determined by using the minimum valley of the first derivative waveform obtained from the step 1003.

Further, the end systolic pressure PES event is determined in step 1006 by using the maximum value of the waveform obtained from step 1001, which is similar to the dot 608 in FIG. 6. In step 1007, the full arterial pulse waveform of the aortic pressure AOP (FAP_aortic) or the pulmonary artery pressure PAP (FAP_pulmonary) from the step 1001 is calculated. In step 1008, the arterio-venous (AV) waveform of the aortic pressure AOP (AV_aortic) or the pulmonary artery pressure PAP (AV pulmonary) from the step 1001 is calculated. In step 1009, the end (the dot 611) of the arterio-venous pulse event of the AV waveform in step 1008 is determined. This AV pulse event becomes zero for that heart cycle, which is substantially coincident in time with the pre-diastolic end-systolic pressure PDPES event, which is the dot 612 in FIG. 6, defined by the ventricular pressure point post completion of the isovolemic relaxation and prior to the onset of diastolic expansion.

Continuing in the process 1000, in step 1010 the Left-Right Balance (LRB) or Right-Left Balance (RLB) parameter is calculated dependent upon if AOP or PAP was used, respectively, in step 1001. This Balance parameter is based upon the respective FAP and AV generated using a transfer function, preferably using the ratio of the AV area under the curve, measured by integration over the cardiac cycle, to FAP area under the curve, measured by integration over the same cardiac cycle, or by some other relating transfer function, from the corresponding steps 1007 and 1008 as well a measurement of the heart rate HR. Whereas the DC offset can be either included, or normalized, or removed by subtraction. In step 1011, the timing of the R-wave event 614 in the QRS segment of the ECG (or EGM) waveform 603, which is substantially coincident with the end diastolic PED event (the dot 607), is determined as illustrated in FIG. 6. The heart rate is also measured in the step 1011. In step 1012, the time difference between the R-wave event 614 in the step 1011 and the valve open event 609 in step 1004 is calculated as a delta T1.

In step 1013, by using the slope of the line segment of the aortic pressure (AOP) (or pulmonary artery pressure (PAP)) pressure between the valve open event 609 and a short time after the valve opening (up to a period of a point approximately mid-way 617 of the maximum AOP (or PAP) pressure). The PED value of the ventricular pressure signal 605 can be extrapolated backwards from the AOP (or PAP) waveform signal 601 (or an estimate of it). The extrapolation period is defined by calculating the time between the ECG R event (614) and the valve open event (609) as delta T1 of step 1012. The extrapolation slope is defined by measuring the linear line fit across the AOP (or PAP) pressure points 609 and the selected point 617. This AOP (or PAP) line segment (x-values representing time, and y-values representing pressure values) is extrapolated backwards in time up to the x-axis point in time to estimate the PED event (the dot 607), as defined by the time occurrence of the R-event of the ECG (or EGM) waveform 603. The y-axis value based upon the result of this extrapolation is the PED pressure value at point 607, which is considered a first static pressure point. For a tiny fraction of a second during the heart cycle, at this first static pressure point, all positive and negative dynamic forces applied on the contained blood volume in the chamber are nulled, and the ventricle is in its largest volume. The first static pressure therefore represents the pressure only due to the volume of the blood in the ventricle at its largest volume.

In step 1014, the time difference between the end of the AV pulse event in the step 1009 and the valve close event in step 1005 is calculated as a delta T2. Next, in step 1015 by using the slope of the line segment of the AOP (or PAP) pressure between the valve close event 610 and a short time before the valve closing (up to a period of a point approximately mid-way 618 of the maximum AOP (or PAP) pressure). The PDPES value of the ventricular pressure can be extrapolated forward from the measured AOP (or PAP) pressure (or an its estimate of it). The extrapolation period is defined by calculating the time between the end of AV pulse event (611) and the valve close event (610) as delta T2 of step 1014. The extrapolation slope is defined by measuring the linear line fit across the AOP (or PAP) pressure points 610 and the selected point 618. This AOP (or PAP) line segment (x-values representing time, and y-values representing pressure values) is extrapolated forward in time up to the x-axis point in time to estimate the PDPES event, as defined by the time occurrence of the small peak 615 in the first derivative (waveform 602) of the AOP (or PAP) pressure post the valve close event. The y-axis value based upon the result of this extrapolation is the PDPES pressure value at point 612, which is considered a second static pressure point. For a tiny fraction of a second during the heart cycle, at this second static pressure point, all positive and negative dynamic forces applied on the contained blood volume in the chamber are nulled, and the ventricle is in its smallest volume. The second static pressure therefore represents the pressure only due to the volume of the blood in the ventricle at its smallest volume.

In another aspect of the present invention, the inventor has realized that the variability of the Balance parameter (LRB or RLB) is a viable indicator of cardiac health state. The balance parameter is a very sensitive and specific measure for pulse variability, reflecting variation in supply and demand of blood, rather than the variation in the blood pressure or flow alone. It is also sensitive enough to detect respiration modulation effect of the cardiac cycle and advantageously allows the detection of respiration rate and parameters directly from the balance parameter variations.

With reference now to FIGS. 7(*a*) and, 7(*b*), there are shown a balance parameter indication with a plurality of auto-regulation cycles modulating a plurality of respiratory cycles 701. Each point on the plot is a cardiac cycle. The portion of the respiratory cycles 701 between the points A and B in FIG. 7(*a*) are expanded and enlarged in FIG. 7(*b*). The boxed area 702 in FIG. 7(*b*) is the auto-regulation cycle, and the boxed area 703 is the respiratory cycle. Thus, in this aspect of the present invention, the respiration rate is detected from simple variation cycle of the balance parameter. Furthermore, the Balance parameter is sensitive enough to detect the cardiac auto-regulation cycle 702 which maintains the regulation of the balance between the left and right cardiac outputs. This longer period regulation cycle 702 was previously not measurable or realizable, but is now advantageously detected by the balance parameter of the instant invention. Characterization of auto-regulation function is therefore an important aspect of this invention. Detection of abnormalities in the auto-regulation function and its cycle characteristics, alarming against auto-regulation abnormalities, and display and communication of auto-regulation information to users are all part of the instant invention.

Figure 8A:
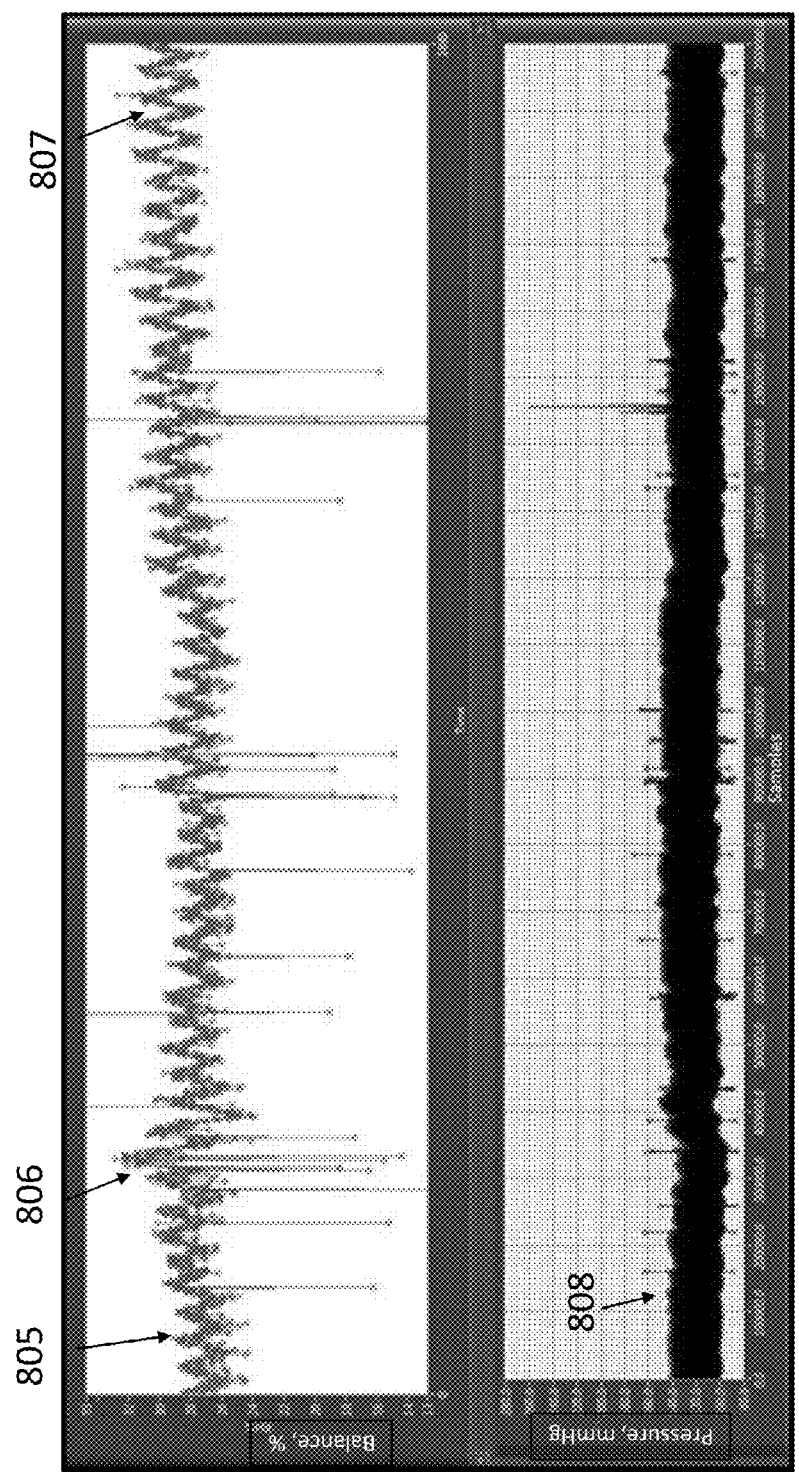
FIG. 8(a) depicts balance parameter waveforms useful in depicting the respiratory cycle and the normal cardiac auto-regulation function cycle, and 8(b) depicts disappearance of cardiac auto-regulation due to abnormal heart conditions, whereby its restoration is necessary for indicating restoration of normal heart condition.

With reference to FIG. 8(*a*), there is depicted the normal auto-regulation function to the cardiac cycle 805 as a vital indicator to the health state of the heart. Biased balance indication (i.e. too high, or too low) is an early indicator of heart disease. In FIG. 8(*b*), there is also depicted a perturbation at 806 causing the balance parameter to start an increasing trend 806 through 807, which is not be easily detectable using blood pressure signal alone. As shown in FIG. 8(*b*), when the heart experiences abnormal ischemia 811 the auto-regulation periodic cycle pattern of the balance parameter disappears 813, and when arrhythmia or fibrillation is experienced 812 a high variance of the balance parameter is indicated. Abnormal cardiac conditions such as arrhythmia or fibrillation are detected with the variance of the balance parameter above a threshold and can be indicated for an alarm. Restoration of auto-regulation periodic cycle is an essential indication of restoration of normal function to cardiac cycle. Absence of auto-regulation or other abnormal cardiac conditions are detected with the variance of the balance parameter below a threshold and can be indicated for an alarm. Abnormal cardiac condition detection and indication can be used for closed loop feedback in the delivery of therapeutic medications or to invoke therapy using a pacemaker, cardioverter, or a defibrillator.

Figure 12:
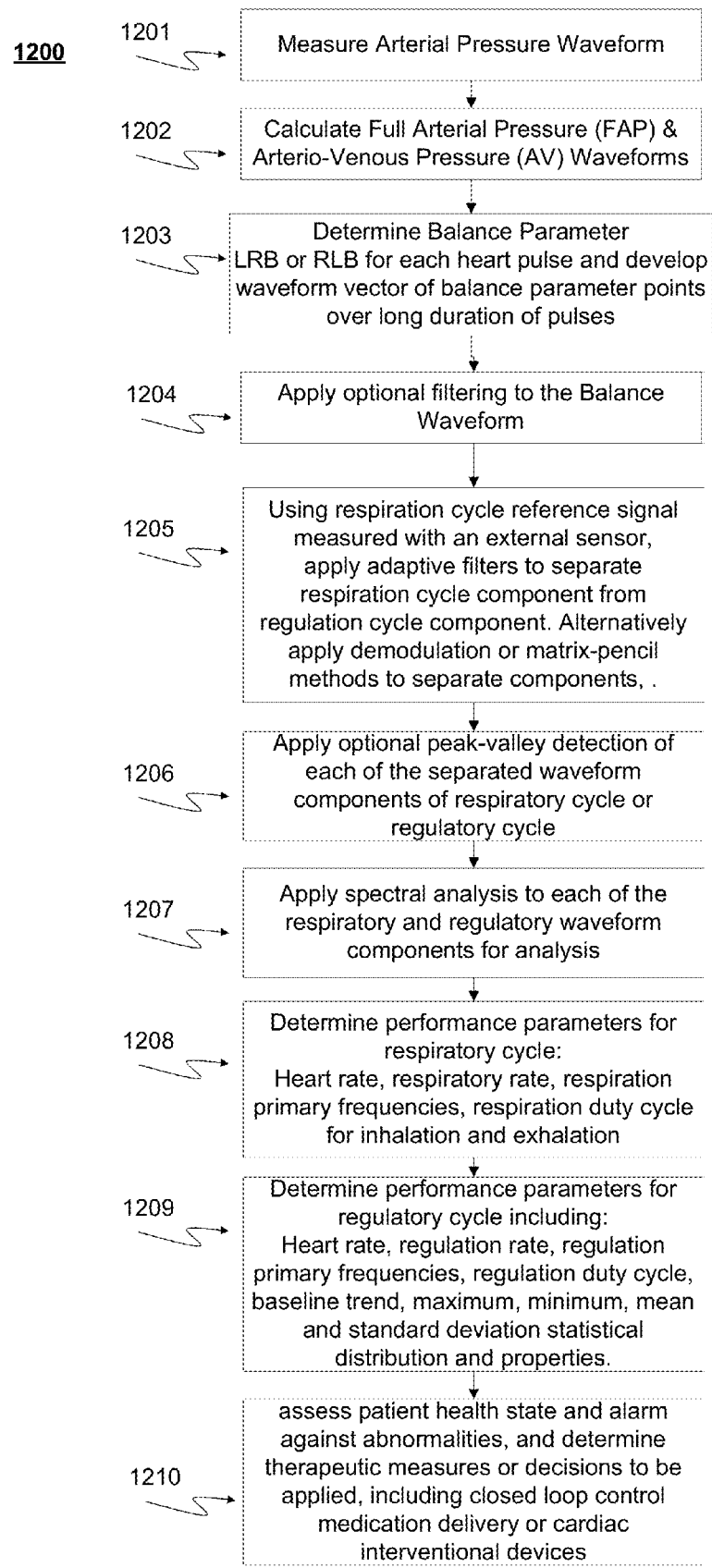
FIG. 12 is a flow chart of an exemplary embodiment of the method of FIG. 8 for using the balance parameter for measurement of the cardiac regulation cycle.

With reference to FIG. 12, there is illustrated a flow chart 1200 of an exemplary embodiment of the method of FIGS. 7 and 8 for using the balance parameter for measuring the cardiac regulation cycle. By separating the respiration signal component 703 from the regulation signal component 702, it is possible to obtain a better assessment of each of the individual components independently.

In the process 1200, in the step 1201 an arterial pressure waveform (i.e., from an peripheral artery or pulmonary artery or aortic artery) is measured initially. In step 1202, a full arterial pulse (FAP) and an arterio-venous (AV) pulse are calculated. In step 1203, the balance parameter (LRB or RLB) is determined for each of heart pulse over a long duration of the heart pulses. In step 1204, there is applied optionally a filtering to smooth out the balance parameter from step 1203. In step 1205, demodulation of the respiratory signal carrier is applied to obtain the regulatory signal carrier, or alternately demodulation of the regulatory signal carrier is applied to obtain the respiratory signal carrier.

However, this is difficult to achieve effectively since the respiration rate is variable. One preferred method is to use adaptive filters so as to filter out an undesired component (such as either respiration or regulation) in order to obtain the desired component (such as either regulation or respiration, respectively). Adaptive filters require a reference signal to indicate the component to be separated out. This reference signal is more easily provided as the respiratory signal which can measured with a variety of methods, including motion sensitive accelerometers, or tension belt or modulation of the ECG waveforms, or nasal air flow sensor. Also, there are conventional tools known in the prior art, such as matrix-pencil methods for frequency estimation, can be used to separate very effectively the component frequencies representing the cardiac auto-regulation cycle from the respiration cycle.

In step 1206, a peak-valley detection is optionally applied to the separated components from step 1205 to determine the end-of-cycle period, frequency, and duty cycle. Spectral frequency analysis (e.g. Fourier series) is performed in step 1207 to detect the primary regulation and respiration rate. In step 1208, other respiratory parameters can also be derived such as the inhalation and exhalation duty cycle. The detected respiratory rate can be utilized to monitor and provide alert for respiratory disorders, including respiratory apnea in a highly sensitive, specific, and reliable method, that is not affected by additional noise sounds such as snoring or air flow measurement errors. This method can also be combined with anesthesia ventilators in order to determine patient restoration of respiratory function after respiratory depression with anesthesia or pain medications, to allow determination of optimal ventilator settings to wean patient of ventilator and to control the ventilator in closed loop to achieve patient weaning off ventilator. The respiration waveform can also be used to more generally assess patient respiratory function and health state. In step 1209, by using the auto-regulation cycle rate, its period or frequency, or duty cycle, baseline trend, maximum, minimum, mean and standard deviation statistical distribution and properties, and heart rate can all be determined. In step 1210, the auto-regulation cycle and respiratory cycle characteristics and information can be used to assess patient health state and alarm against abnormalities, and determine therapeutic measures or decisions to be applied, including closed loop control of medication delivery or cardiac interventional devices. The balance parameter and auto-regulation performance parameters can be used to optimize the treatment protocol of renal dialysis such controlling the blood flow rate into the dialyzer to avoid abnormal cardiac balance and autoregulation performance. The balance parameter and auto-regulation performance parameters can also be used in feedback closed loop control of dialysis devices to achieve optimal dialysis treatment control. The balance parameter and auto-regulation performance can also be used for detection and alarming of cardiac stress, patient pain, or surgical nociception, whereby marked trend variations in the balance levels and regulation cycle are associated with elevated pain levels or cardiac stress. The balance parameter and auto-regulation performance parameters can be used to provide feedback control to ventricular assist devices and counterpulsation devices to help optimize the blood flow for a more balanced auto-regulation of the heart cycle. The balance parameter and auto-regulation performance parameters can be also used for guidance and optimization of lead placement locations of a pacemaker system to provide a more balanced auto-regulation performance of the heart cycle. The cardiac balance and autoregulation performance parameters can be used to optimize blood flow between the mother and the fetus and can be used to study the fetus cardiac regulation and balance as well as the mother's cardiac regulation and balance, and the interaction of both over the term of the pregnancy, to ensure that both mother and fetus are receiving optimal blood flow, and to ensure baby healthy rate of growth and nutrition with adequate blood flow. Abnormal fetal blood flow in relationship to mother's blood flow can be detected and alerted.

The variance (or similarly standard deviation) of the Balance parameter has been advantageously found by the inventor to be a strong indicator of the health status of the subject's cardiac function. If the Balance parameter variance is too high as illustrated at 812 in FIG. 8(*b*), then it is an indicator of cardiac instability, potentially as an indicator or measure of surgical nociception or pain, arrythmia, ischemia or myocardial infarction, as some causes for high balance variance. These are typically associated with loss of the auto-regulation function indicated by the balance parameter at 811 and 813. The absolute value of the balance parameter is used as an indicator of cardiac imbalance representing a biased performance toward the left or right heart blood pumping (cardiac output). Such an imbalance can lead to the accumulation of blood in parts of the circulatory system which can lead eventually to cardiac arrhythmia, or heart failure such as congestive heart failure.

If on the other hand the variance of the heart is too low from its normal auto-regulation cycle variance baseline, then this also is an indicator of hydration status or other cardiac problems including, for example hypovolemia, or low hydration or low cardiac output status, and is a strong predictor of heart failure. There exists a margin of normal variance of the Balance parameter about which the cardiac performance is automatically adaptively maintained by the heart during the auto-regulation cycle.

It is still another aspect of this invention to use both the Balance parameter as a mean target value set point and the Balance parameter variance (or standard deviation) margin as a second target set point in control of medication delivery that affect these cardiac performance parameters to the desired set target levels or margins. It is still yet another aspect of this invention is to use the measurement of Balance parameter variance at 812 as well as the absolute value of the Balance parameter at 807 for purposes of monitoring, predicting, and/or alerting against cardiac arrhythmias, fibrillation, ischemia, or heart failure such as congestive heart failure (CHF), or detection of onset of seizures and alarming against it.

In addition, valvular malfunction (regurgitation or insufficiency) will affect the appearance or timing of the Dicrotic Notch. It is thus envisioned that this invention can also use the RLB Balance and/or LRB Balance parameters to diagnose the presence or absence of as well as the degree or status of valvular regurgitation or insufficiency. Furthermore, another aspect of this invention is to use the balance parameter for indication of valve regurgitation or insufficiency.

Further, a cardiovascular control support system that provides pumping of a balloon in order to displace blood volume whereby the device is placed in a vascular artery or vein is used to achieve therapeutic or optimal Right-Left Balance levels. Another aspect of this invention is to use the Balance parameter as a process variable in a closed loop control system for controlling a counter pulsation (balloon) apparatus in order to achieve a desired set target value for cardiac parameters, including Balance parameter, blood pressure, and blood flow rate or cardiac output. A model predictive controller (MPC) or a model free adaptive controller can be preferably used for this purpose.

In yet another embodiment of the present invention, an estimated aortic pressure waveform can be derived by first estimating its components of FAP_aortic and AV_aortic and then subtracting the estimated AV_aortic waveform from the estimated FAP_aortic waveform. In FIG. 9, there is depicted a flow chart 900 of an exemplary technique for determining the estimated aortic pulse waveform, defined by one of aortic blood pressure, blood flow rate, and blood constituent concentration. Initially, at step 901 the aortic pulse is measured. Simultaneously, at step 904 the (peripheral) arterial pulse (e.g., radial or femoral or carotid) is measured, defined by one of arterial blood pressure, blood flow rate, and blood constituent concentration. In step 902, the aortic's full arterial pulse (FAP_aortic) waveform is computed as defined herein. Similarly, the peripheral artery's full arterial pulse (FAP_arterial) is computed in step 905. Further, the aortic arterio-venous pulse (AV_aortic) is computed in step 903. The (peripheral) arterial arterio-venous pulse (AV_arterial) is computed in step 906.

In step 907, the relationship or transfer function between the FAP_arterial as input and the FAP_aortic as output can be defined using many modeling and adaptive methods, including a system identification method, as mentioned herein, preferably using linear system identification producing a state-space linear model to define such transfer function. In one preferred embodiment, the mapping between FAP_arterial and the FAP_aortic, the transformation's transfer function (preferably state-space model's coefficients) can be identified easily. Such model creates a calibration transfer function when both FAP_arterial and FAP_aortic are available. In step 909, such calibration transfer function can then be used with input FAP_arterial to produce a more accurate estimate of the output FAP_aortic. Similar or equivalent steps can be taken as above with FAP_pulmonary derived from the pulmonary artery pulse replacing the FAP_aortic, defined by one of pulmonary artery's blood pressure, blood flow rate, and blood constituent concentration.

Continuing in the process 900, in the step 908 the (peripheral) arterial pulse (radial or femoral or carotid) arterio-venous pulse (AV_arterial) as defined herein, is used to estimate the aortic's arterio-venous pulse (AV_aortic) waveform as defined above. The relationship or transfer function between the AV_arterial as input and the AV_aortic as output can be defined using many modeling and adaptive methods, including a system identification method, as mentioned herein, preferably using linear system identification producing a state-space linear model to define such transfer function. In one preferred embodiment, the mapping between AV_arterial and the AV_aortic, the transformation's transfer function (preferably state-space model's coefficients) can be identified easily. Such model creates a calibration transfer function when both AV_arterial and AV_aortic are available. In step 910, such calibration transfer function can then be used with input AV_arterial to produce a more accurate estimate of the output AV_aortic. Similar or equivalent steps can be taken as above with AV pulmonary derived from the pulmonary artery pulse replacing the AV_aortic. Finally, in step 911 an estimate of the aortic pulse waveform can be derived by subtracting the estimated AV_aortic waveform from the estimated FAP_aortic waveform.

Figure 11:
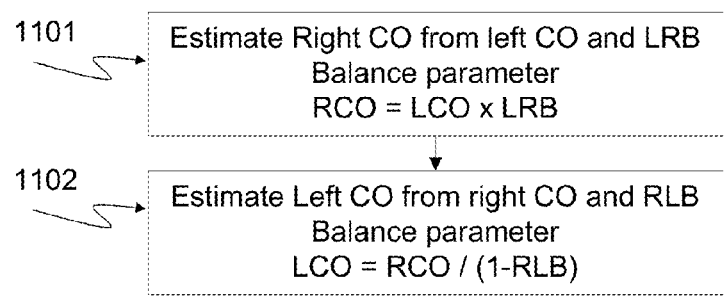
FIG. 11 is a flow chart of an exemplary embodiment of the method for estimating a second ventricular chamber's performance based upon information from a first ventricular chamber.

With reference to FIG. 11, there is shown a flow chart 1100 of an exemplary embodiment for estimating the other ventricular chamber's performance based upon information from the one ventricular chamber. The left heart's (VED−VES) is estimated, on average, using a Balance adjusted right cardiac output (RCO) divided by the heart rate (HR). If measured cardiac output is performed in the right heart, the volume difference (VED−VES)=RCO/HR. The parameter RCO can be adjusted using the Balance parameter value (Left-Right Balance (LRB) from any aortic branch artery or Right-Left Balance (RLB) from any pulmonary branch artery) for the estimation of the left heart's cardiac output LCO.

In step 1102 of FIG. 11, the left ventricle's (LV) cardiac output is calculated as either LCO=(RCO/LRB) or LCO=RCO/(1−RLB). Similarly, in step 1101 the right ventricle's (RV) cardiac output is calculated as either RCO=LCO*LRB or RCO=LCO*(1−RLB). Both LRB and RLB are <1.0, but the LCO will be greater than the RCO, with the difference being attributed to inefficiencies of transfer (e.g. backflow portion or tissue fluidic uptake). A higher RLB is associated with a lower LRB and is typically associated with left heart abnormal function. Similarly, a lower RLB is associated with a higher LRB and is typically associated with right heart abnormal function.

Summarizing the above description of the present invention with respect to FIGS. 9 and 10, a plurality of peripherally measured arterial pulse in step 904 is used to derive a FAP_arterial waveform in step 905, and a main artery (aortic or pulmonary artery) measured arterial pulse in step 901 is used to derive its FAP in step 902. Then, applying a calibration step, the plurality of input derived (peripheral)-arterial waveform(s) is/are mapped to output primary main artery FAP_aortic (or FAP_pulmonary) using a transfer function defined by a system identification method at respective steps 907 and 908. Preferably, the system identification method is a linear state-space model in a MISO (multi-input single-output) or SISO (single-input single-output) configuration.

Then, in the steps 909 and 910, there is provided continuously acquiring (peripheral) arterial pulse, deriving the FAP_arterial and employing the previously identified transfer function to produce an estimate of the FAP_aortic. In the step 911, there is provided using the continuously produced estimate of the FAP_aortic to estimate the left ventricular (LV) pressure points of PED and PDPES obtained from the process 1000. Equivalently, there is provided using the continuously produced estimate of the FAP_pulmonary to estimate the right ventricular (RV) pressure points of PED and PDPES.

In the process steps of FIG. 10(b), there is provided using the PED and PDPES estimated in conjunction with measured or estimated (adjusted) cardiac output and heart rate and Balance parameter to produce cardiac parameters including, but not limited to, absolute values of end-diastolic volume, end-systolic volume, and additional cardiac parameters known-in-the-art such as stroke volume, cardiac output, ejection fraction, systemic vascular resistance, contractility, and stroke work. Furthermore, there is produced an estimate or measurement of the duration of the ventricular iso-volemic contraction period and the ventricular iso-volemic relaxation period.

Figure 13:
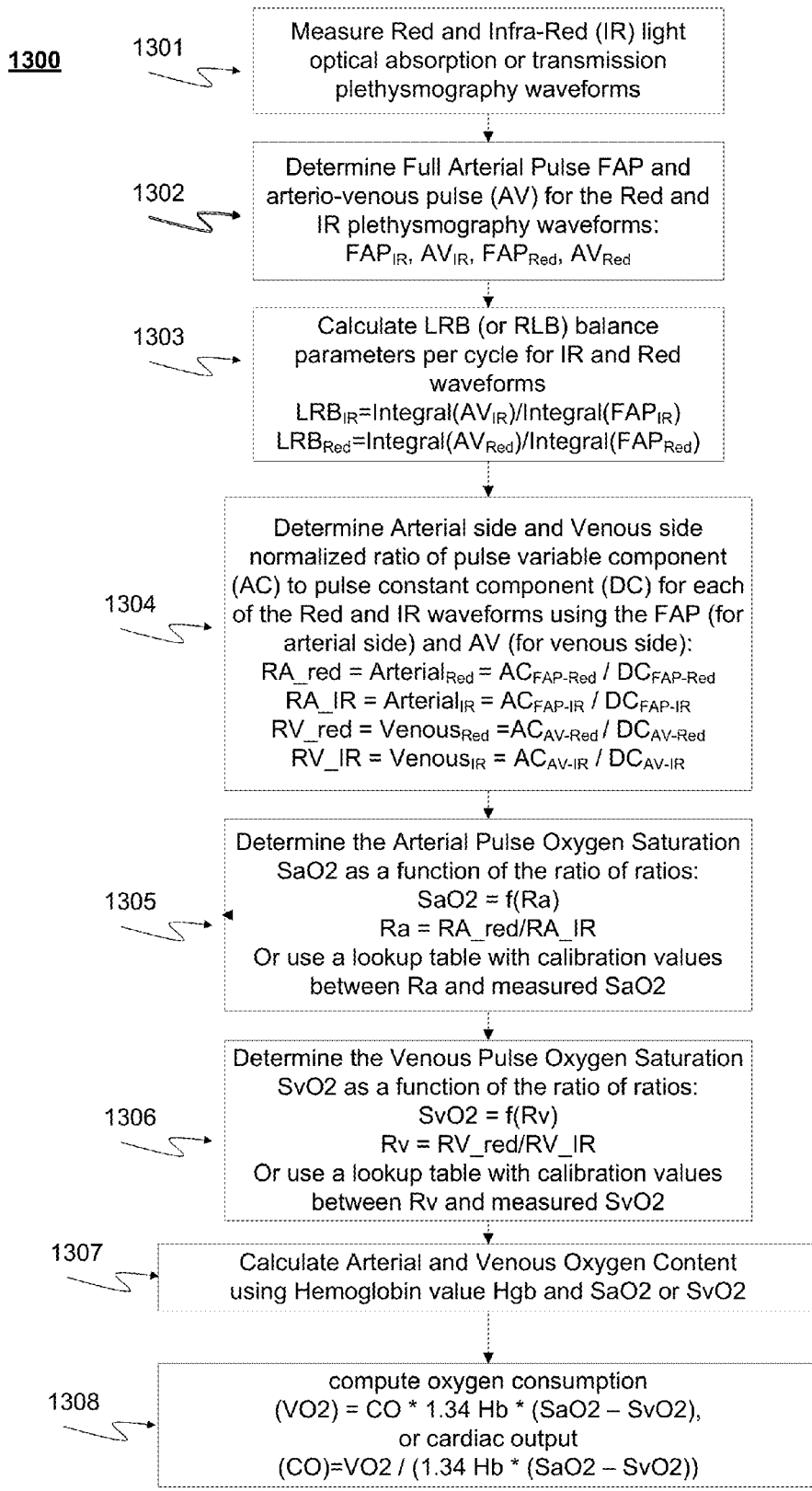
FIG. 13 is a flow chart of an exemplary embodiment of the method for calculating the arterial and venous pulse oximetry based upon full arterial pulse FAP and arterio-venous pulse AV.

Referring now to FIG. 13 of the drawings, there is depicted a flow chart 1300 of an exemplary embodiment of the present invention for calculating the arterial and venous side oximetry based upon FAP and AV. Traditionally, oximetry methods were limited to arterial side oxygen measurements and not venous side because of the reliance on pulse variable component as representative of the arterial oxygen contribution to the measured optical signal. The inventor's realization of the arterio-venous pulse (AV) and full arterial pulse (FAP) as differentiated concepts from the typically measured raw arterial pulse enables beneficially measurement of the venous side oxygen content or saturation and thus represent other aspects of this invention.

Initially, in step 1301 of the process 1300, using known in the art methods, a plethysmography waveform, preferably infra-red and red optical in either absorbance or transmission modes, is measured which is representative of an arterial pulse by using conventional prior art methods. In a second step 1302, the FAP (full arterial pulse) and AV (arterio-venous) pulses for both the red and infrared plethysmography waveforms in the step 1301 is determined. In an optional step 1303, the calculation of the LRB or RLB balance parameters per cardiac cycle using the FAP (full arterial pulse) or AV (arterio-venous pulse) pulses as source signals. Either the red or infra-red source plethysmography can be used or both of them can be used in order to obtain a secondary measurement. Whereas the balance parameter is computed as a transfer function relationship between the AV and FAP. In one embodiment the transfer function represents the ratio of the integral of the AV pulse to the integral of the FAP pulse. In another embodiment the transfer function represents the state space linear system identified using system identification methods.

The venous pulse has traditionally been considered too difficult to measure and the plethysmograph pulse was attributed mostly to arterial pulse and therefore the measured pulse was used only for arterial oximetry. In this present invention, we separated the measured arterial pulse is separated from the derived venous pulse by using the full arterial pulse (FAP) concept. Therefore, calculation of venous side oximetry can similarly be accomplished using the arterio-venous (AV) pulse portion. The arterio-venous (AV) pulse can be directly estimated or indirectly computed by subtraction of the raw measured arterial pulse plethysmograph portion from the full arterial (FAP) pulse.

In a subsequent step 1304, the arterial side oximetry is calculated using full arterial pulse (FAP), which uniquely accounts for the venous pulsation effect on arterial oximetry, as represented by the arterio-venous (AV) pulse contribution. Known-in-the-art oximetry computational methods are applied on a uniquely different input signal (from prior art), namely the FAP pulse, to compute the ratio R of the variable (AC) component normalized to the constant (DC) component of the waveform to give R_Arterial (RA)=AC_FAP/DC_FAP. Similarly, known-in-the-art oximetry computational methods are applied on a uniquely different input signal (from prior art), namely the AV pulse, to compute the ratio R of the variable (AC) component normalized to the constant (DC) component of the waveform to give R_Venous (RV)=AC_AV/DC_AV.

The computations of R_Arterial (RA) and R_Venous (RV) are performed twice, once using the red plethysmograph waveform and another using the infrared plethysmograph waveform. These computational results yield red-light (RA_red, RV_red) and similarly the infra-red light (RA_IR, RV_IR) measured waveforms.

In step 1305, the ratio of the two ratios RA_red/RA_IR then represents a curve that needs to be empirically calibrated to the arterial oxygen saturation values. In the step 1307, the arterial oxygen saturation (or arterial oxygen content is then estimated using a lookup table (or transfer function) from the ratio of the two ratios, as described above, after calibration to saturation values in the range 0-100%. For patients with abnormal health state, this calculation can now be more accurately performed using the calculated full arterial pulse (FAP) as the source signal instead of the raw measured pulse waveform plethysmograph, which may be affected by the contributions of the venous pulsations.

In step 1306, the ratio of the two ratios RV_red/RV_IR then represents a curve that needs to be empirically calibrated to the venous oxygen saturation values. The venous oxygen saturation (or venous oxygen content in the step 1307 is calculated from a lookup table (or a transfer function) from the ratio of the two ratios, as described above, after calibration to saturation values in the range 0-100%.

Also, in the step 1306, a measurement or calculation of arterial pulse oxygen saturation SaO2 is provided, using the previously described full arterial pulse (FAP). Then, in the step 1307 a measurement or calculation of the venous pulse oxygen saturation SvO2 is simultaneously provided, using the arterio-venous pulse (AV). In the step 1308, the known Fick principle equation is used to compute oxygen consumption (VO2)=CO*1.34 Hb*(SaO2−SvO2), or cardiac output (CO)=VO2/(1.34 Hb*(SaO2−SvO2)), where Hb is hemoglobin value. CO is preferably estimated using aforementioned methods of estimating PED and PDPES, as described in FIGS. 10 and 11. This is valid when pulmonary blood flow is balanced, or approximately identical, to systemic blood flow for an equivalent LRB and RLB. The relationship between the LRB and RLB can be estimated to be complimentary to 100% (i.e LRB=1−RLB), but is best measured using individual left and right heart pressure waveforms to detect shifts and delays in the LRB parameter or the RLB parameter thus affecting the systemic-pulmonary balance. Systemic-pulmonary blood flow circulation balance can be measured as a ratio LRB/RLB. More generally, systemic-pulmonary balance is modeled as a transfer function relationship, preferably, using a state space linear model of the between LRB (as input or output) to the RLB (as output or input, respectively). Such state space model coefficients and order can be estimated using system identification methods, and its characteristic state variables, poles, and zeros can be used to quantify the systemic-pulmonary balance parameter.

This invention advantageously enables simultaneous measurement or calculation of the arterial SaO2 and venous SvO2 blood (using the process 1300), and the cardiac output CO (using the process 1000*a*). Given a known or measured SaO2, SvO2, CO, and a hemoglobin Hg value, in steady state (i.e., relatively constant), one can continuously compute and monitor the oxygen consumption (uptake) (VO2). Oxygen consumption and cardiac output monitoring are especially critical in Sepsis disease state for monitoring the health state of the patient. Oxygen consumption, is in ml of pure gaseous oxygen per minute. This may be measured with more difficulty using a spirometer within a closed rebreathing circuit incorporating a CO2 absorber. The present invention allows an advantageous and more accurate measurement method of oxygen consumption.

In another embodiment, if VO2 and Hb are known or measured, this invention enables the use of simultaneous full arterial pulse and arterio-venous pulses to estimate the arterial and then venous oxygen saturation and then use in calculation of the cardiac output.

Turning now to FIG. 14, there is illustrated a flow chart 1400 of an exemplary embodiment of the present method for calculating of the oximetry relationship using the red-light and infra-red light plethysmograph waveforms. In step 1401, linear system identification methods, preferably linear state-space model (of any order), are utilized to relate the full arterial pulse measured in the red light (as input or output) with the full arterial pulse measured in the infrared light (as output or input, respectively) wherein the linear state-space model coefficients are identified using known in the art adaptive system identification methods. In step 1402, the arterial oxygen saturation and arterial oxygen content values are determined as a function of the linear state-space model's poles and zeros locations (i.e., z-plane location distribution and centroid), state variables, and gain values and can be mapped using either a lookup table or a transfer function after calibration to saturation values 0-100%.

As a consequence, the traditional problems encountered in pulse oximetry such as motion artifacts affecting the ratio calculation will advantageously not affect the system state-space model's poles or zeros locations, and gains. Therefore, its derived arterial oxygen saturation or content values will be stable or insensitive to motion artifacts, as such transient noise at the input of the state-space model will be passed to the output, and only systematic relationships between the red and infra-red will be represented by the model's poles and zeros and gain values.

In step 1403, a system identification state-space model is used to relate the arterio-venous pulse measured in the red light (as input or output) with the arterio-venous pulse measured in the infrared light (as output or input, respectively). In step 1404, the venous oxygen saturation and venous oxygen content values are determined as a function of the linear state-space model's poles and zeros locations (i.e., z-plane location distribution and centroid), state variables, and gain values and can be mapped using either a lookup table or a transfer function after calibration to saturation values 0-100%. Again, the traditional problems discussed above will be thus overcome.

It should be readily obvious that the use of the raw measured arterial pulse from red and infrared lights plethysmograph to identify a relationship using a linear transfer function, preferably state space, using system identification methods is also possible to obtain arterial oxygen saturation or venous oxygen saturation values. Oxygen saturation values are determined as a function mapping the linear state-space model's poles and zeros locations, or characteristic state variables, and gain values to oxygen saturation levels. Such mapping function can use either a lookup table or a secondary transfer function after calibration to saturation values 0-100%.

It shall be noted that, in a more generalized sense, an object of this invention is to use linear state-space model transfer function to represent the relationship between two or more light waveforms of a plethysmograph, preferably at wavelengths from ultra-voilet to infrared range, presented to the blood and measured by reflectance or transmission to assess spectral energy absorbance, to measure at least one desired blood constituent concentration as represented in the identified state-space model characteristics and parameters in terms of state space variables or model coefficients. Such desired blood constituent concentration include, but are not limited to, oxygen, carbon dioxide, glucose, and hemoglobin concentration.

From the foregoing detailed description, it can thus be seen that the present invention provides a system for measuring of cardiac blood flow balance parameter between the right chamber of the heart and the left chamber of the heart which includes a sensor device for measuring one of blood pressure and blood flow rate and blood constituent concentration of a patient so as to generate an arterial pulse signal. A processing unit is responsive to the arterial pulse signal for generating a full arterial pulse (FAP) signal, an arterio-venous (AV) pulse signal, and a balance parameter. A computational device is responsive to the balance parameter for further generating a set of physiological parameters. A display station device is responsive to the set of physiological parameters from the computational device for displaying meaningful information.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

APPENDIX

References

1. System Identification: Theory for the User, Lennart Ljung, Prentice Hall, 2nd edition, 1999.
2. System Identification: A Frequency Domain Approach. Rik Pintelon and Johan Schoukens Wiley-IEEE Press, 1st edition, January, 2001
3. Blind Equalization and System Identification: Batch Processing Algorithms, Performance and Applications, Springer, 1st Edition, January 2006.
4. Linear estimation, Kailath, Sayed, Hassibi. Prentice Hall, 2000.
5. Multivariable System Identification For Process Control, Y. Zhu, Elsevier Science; 1 edition (October, 2001)
6. Modeling of Dynamic Systems, L. Ljung, Prentice Hall; 1 edition, May 1994.

The invention claimed is:

1. A method for determining arterial and venous side oximetry based upon full arterial pressure pulse waveform and arterio-venous pressure pulse waveform, comprising the steps of:
    measuring of plethysmography waveforms of red and infra-red lights which are representative of arterial pulses measured by any of optical absorption or transmission by using a non-invasive sensor device configured to be disposed on a portion of the body of a patient, the measured arterial pulses containing mixed interactions of arterial and venous pulsations with the effect of atrial diastolic blood flow demand;
    determining an estimated full arterial pulse waveform representing only a supply side pulse of the left ventricle and defined as the measured arterial pulse signal without the effect of atrial diastolic blood flow demand that reduces the ventricular supply causing a dicrotic notch, and an estimated arterio-venous pulse waveform representing only a demand side pulse of the right atrium and estimating the atrial diastolic blood flow demand as sensed from the arterial side and defined by subtracting the measured arterial pulse signal from the estimated full arterial pulse waveform, for each of the red and infra-red light plethysmography waveforms by way of a processor unit having its input coupled via an A/D converter to the non-invasive sensor device;
    determining further an arterial side and a venous side pulse variable component and a pulse constant component in the processor unit for each of the red and infra-red light plethysmography waveforms by using the estimated full arterial pulse waveform for the arterial side and the estimated arterio-venous pulse waveform for the venous side;
    determining further an arterial side and a venous side normalized ratio of pulse variable component to pulse constant component in the processor unit for each of the red and infra-red light plethysmography waveforms by using the estimated full arterial pulse waveform for the arterial side and the measured arterio-venous pulse waveform for the venous side;
    determining still further the arterial oxygen saturation as a function of a first ratio of the normalized ratio of the full arterial pulse variable component to the full arterial pulse constant component in the processor unit for the arterial side for the red light plethysmography waveform to the normalized ratio of the full arterial pulse variable component to the full arterial pulse constant component for the arterial side for the infra-red light plethysmography waveform;
    determining still further the venous oxygen saturation as a function of a second ratio of the normalized ratio of the arterio-venous pulse variable component to the arterio-venous pulse constant component in the processor unit for the venous side for the red light plethysmography waveform to the normalized ratio of the arterio-venous pulse variable component to the arterio-venous pulse constant component for the venous side for the infra-red light plethysmography waveform; and
    coupling a display station to an output of the processor unit for receiving the arterial oxygen saturation and the venous oxygen saturation and for providing visual and audio monitoring of the patient's health condition and for alerting medical personnel of changes in the patient's health condition.

2. A method for determining arterial and venous side oximetry as claimed in claim 1, further including the step of calculating of one of Left-Right balance parameter between left ventricular blood supply and right atrial blood demand, defined by the arterial pulse measured at one of an aorta and one of its arterial branches, and Right-Left balance parameter between right ventricular blood supply and left atrial blood demand, defined by the arterial pulse measured at one of a pulmonary artery and one of its arterial branches, for each of the red and infra-red light plethysmography waveforms.

3. A method for determining arterial and venous side oximetry as claimed in claim 2, wherein the Left-Right balance parameter $LRB_{red}$ between left ventricular blood supply and right atrial blood demand for the red light per cardiac cycle is defined as a function of $AV_{red}$ and $FAP_{red}$, where $AV_{red}$ is an integral of the arterio-venous pulse waveform and $FAP_{red}$ is an integral of the full arterial pulse waveform for the red light plethysmography waveform of the aorta or any of its arterial branches.

4. A method for determining arterial and venous side oximetry as claimed in claim 2, wherein the Left-Right balance parameter $LRB_{ir}$ between left ventricular blood supply and right atrial blood demand for the infra-red light per cardiac cycle is defined as a function of $AV_{ir}$ and $FAP_{ir}$, where $AV_{ir}$ is an integral of the arterio-venous pulse waveform and $FAP_{ir}$ is an integral of the full arterial pulse waveform for the infra-red light plethysmography waveform of the aorta or any of its arterial branches.

5. A method for determining arterial and venous side oximetry as claimed in claim 2, wherein the Right-Left balance parameter $RLB_{red}$ between right ventricular blood supply and left atrial blood demand for the red light per cardiac cycle is defined as a function of $AV_{red}$ and $FAP_{red}$, where $AV_{red}$ is an integral of the arterio-venous pulse waveform and $FAP_{red}$ is an integral of the full arterial pulse waveform for the red light plethysmography waveform of the pulmonary artery or any of its arterial branches.

6. A method for determining arterial and venous side oximetry as claimed in claim 2, wherein the Right-Left balance parameter $RLB_{ir}$ between right ventricular blood supply and left atrial blood demand for the infra-red light per cardiac cycle is defined as a function of $AV_{ir}$ and $FAP_{ir}$, where $AV_{ir}$ is an integral of the arterio-venous pulse waveform and $FAP_{ir}$ is an integral of the full arterial pulse waveform for the infra-red light plethysmography waveform of the pulmonary artery or any of its arterial branches.

7. A method for determining arterial and venous side oximetry as claimed in claim 1, further including the step of calculating arterial and venous oxygen content in the processor unit by using Fick's equation.

* * * * *